Figure 1A:
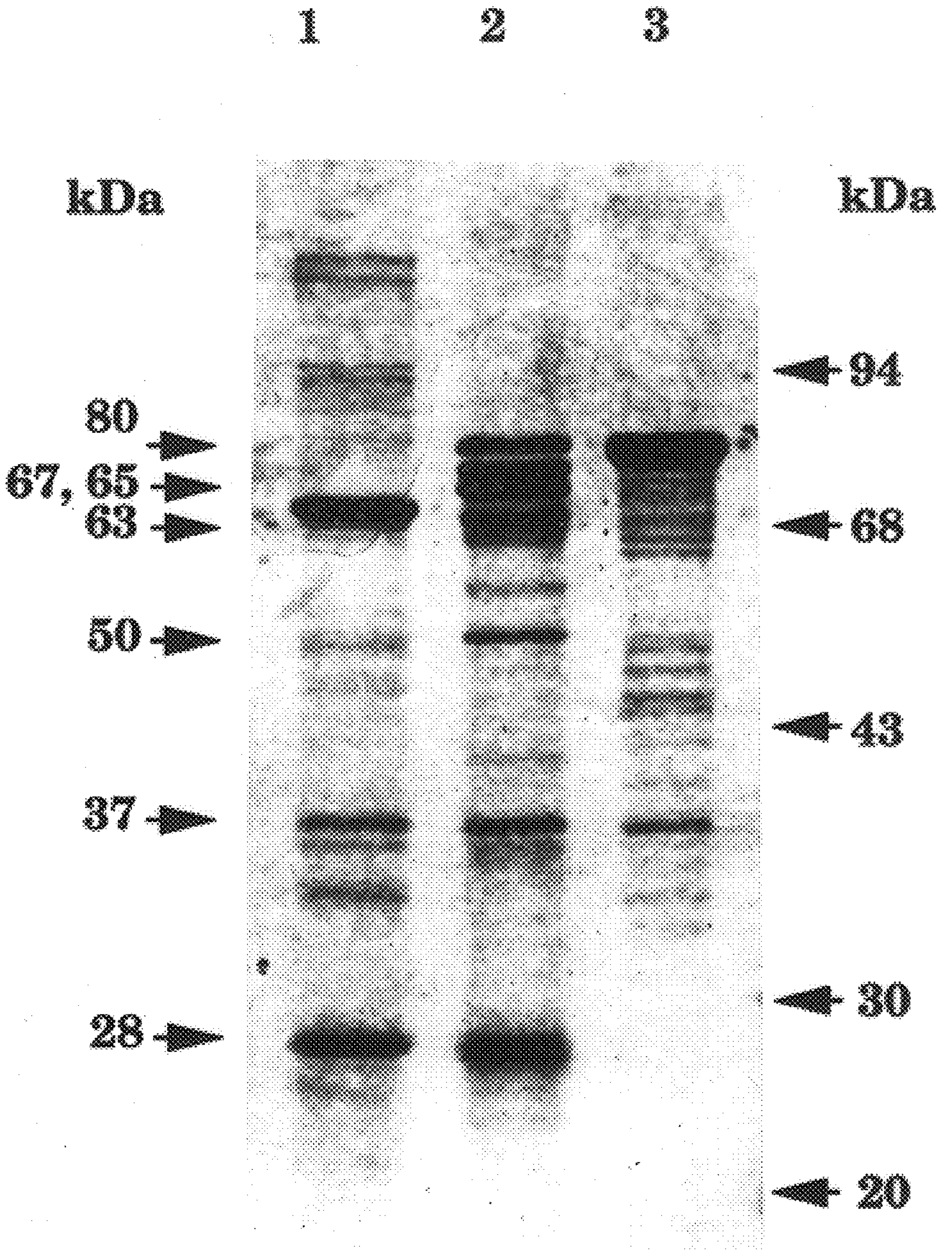

US006071877A

United States Patent [19]

Delecluse et al.

[11] Patent Number: 6,071,877

[45] Date of Patent: Jun. 6, 2000

[54] POLYPEPTIDES HAVING A TOXIC ACTIVITY AGAINST INSECTS OF THE DIPTERAE FAMILY

[75] Inventors: Armelle Delecluse, Thiers-sur-Theve; Isabelle Thiery, Chatillon, both of France

[73] Assignee: Institut Pasteur, Paris Cedex, France

[21] Appl. No.: 08/793,331

[22] PCT Filed: Aug. 24, 1995

[86] PCT No.: PCT/FR95/01116

§ 371 Date: May 13, 1997

§ 102(e) Date: May 13, 1997

[87] PCT Pub. No.: WO96/06171

PCT Pub. Date: Feb. 29, 1996

[30] Foreign Application Priority Data

Aug. 25, 1994 [FR] France .................................. 94 10299

[51] Int. Cl.$^7$ ............................ A61K 38/00; C07K 1/00; C07H 21/04; C12N 15/00

[52] U.S. Cl. ......................... 514/12; 530/350; 536/23.71; 536/23.1; 435/252.3; 435/254.2; 435/320.1

[58] Field of Search .......................... 530/350; 536/23.7, 536/23.71; 514/12; 435/252.3, 254.2, 320.1

[56] References Cited

FOREIGN PATENT DOCUMENTS

| | | |
|---|---|---|
| 0 216 481 | 4/1987 | European Pat. Off. . |
| 0 480 762 | 4/1992 | European Pat. Off. . |
| WO 89/07605 | 8/1989 | WIPO . |

OTHER PUBLICATIONS

Creighton. Proteins: Structures and Molecular Properties, 2nd edition. WH Freeman and Company, New York, pp. 23–28, 1993.

Kawalek et al. Isolation and identification of novel toxins from a new mosquitocidal isolate from Malaysia, *Bacillus thuringiensis* subsp. *jegathesan*. Appl. Envrion. Microbiol. 61(8):2965–2969, Aug. 1, 1995.

Arantes et al. Construction of cloning vectors for *Bacillus thuringiensis*. Gene 108:115–119, 1991.

Donovan et al. Molecular characterization of a gene encoding a 72–kilodalton mosquito–toxic crystal protein from *Bacillus thuringiensis*. J. Bacteriol. 170:4732–4738, 1988.

Yong–man YU, et al., Appl. Environ. Microbiol., vol. 57, No. 4, pp. 1075–1081, "Characterization of Mosquitocidal Activity of *Bacillus thuringiensis* Subsp. *Fukuokaensis* Crystal Proteins", Apr. 1991.

HL Lee, et al., Southeast Asian J Trop. Med. Public Health, vol. 21, No. 2, pp. 281–287, "Isolation of Indigenous Larvicidal Microbial Control Agents of Mosquitos: The Malaysian Experience", Jun. 1990.

Michael D. Kawalek, et al., Appl. Environ. Microbio., vol. 61, No. 8, pp. 2965–2969, "Isolation and Identification of Novel Toxins From a New Mosquitocidal Isolate From Malaysis, *Bacillus shuringiensis* Subsp. *jegathesan*", Aug. 1995.

Armelle Delecluse, et al., Appl. Environ. Microbiol., vol. 61, No. 12, pp. 4230–4235, "Cloning and Expression of a Novel Toxin Gene From *Bacillus thuringiensis* Subsp. *jegathesan* Encoding a Highly Mosquitocidal Protein", Dec. 1995.

*Primary Examiner*—Karen Cochrane Carlson
*Assistant Examiner*—Devesh Srivastava
*Attorney, Agent, or Firm*—Oblon, Spivak, McClelland, Maier & Neustadt, P.C.

[57] ABSTRACT

The invention relates to a sequence of nucleotides characterized in that it corresponds to the fragment HindIII of about 4.3 kb which can be obtained from the plasmid pJEG80.1 which has been deposited at the CNCM on Aug. 23, 1994 with the number I-1469 or capable of hybridizing in stringent conditions with said plasmid. It also relates to polypeptides resulting from the expression of said sequence and their utilization in toxic compositions against insects.

21 Claims, 20 Drawing Sheets

FIG. 4A(1)

```
2/1                                     32/11
GAT GTG AGG ATT ATT ACG TGA ATA CTG ATT ATG ATA ATT TTG AAA AGA AAT CAT ATT TGC

62/21                                   92/31
AAC CAG AAT CAT CAT ATG ATT ACA TGT CAG AAG AAA ATC ACA AAG TTC CAT TAA TTA GAT

122/41                                  152/51
GTG AAT TCC TAT TTT TAT TTC AGT CCA GAA TCC TGA ATA ATG GAA ATT AAA TGC ACC CTA

182/61                                  212/71
TGA TTT ATA AAT ATA TGT ACC TTT AAA ACA AGA ATA ATT ATA ACT GTA TAA AAA TAG GTA

242/81                                  272/91
TAC TAT TGG AAA ACA AAA AAG TTA ATT ATG AAA AGA TTT CGT TTA TAT TAG TAA ATT GTT

302/101                                 332/111
TAA AGA AGA GGG GGC ATG TTT TAA ATG CAA AAT AAC AAC TTT AAT ACC ACA GAA ATT AAT
                                met gln asn asn asn phe asn thr thr glu ile asn
```

FIG. 4A(2)

```
362/121                                 392/131
AAT ATG ATT AAT TTC CCT ATG TAT AAT GGT AGA TTA GAA CCT TCT CTA GCT CCA GCA TTA
asn met ile asn phe pro met tyr asn gly arg leu glu pro ser leu ala pro ala leu
422/141                                 452/151
ATA GCA GTA GCT CCA ATT GCT AAA TAT TTA GCA ACA GCT CTT GCT AAA TGG GCT GTA AAA
ile ala val ala pro ile ala lys tyr leu ala thr ala leu ala lys trp ala val lys
482/161                                 512/171
CAA GGG TTT GCA AAA TTA AAA TCC GAG ATA TTC CCC GGT AAT ACG CCT GCt ACT ATG GAT
gln gly phe ala lys leu lys ser glu ile phe pro gly asn thr pro ala thr met asp
542/181                                 572/191
AAG GTT CGT ATT GAG GTA CAA ACA CTT TTA GAC CAA AGA TTA CaA GAT GAC AGA GTT AAG
lys val arg ile glu val gln thr leu leu asp gln arg leu gln asp asp arg val lys
602/201                                 632/211
ATT TTA GAA GGT GAA TAC aAA GGA ATT ATT GAC GTG AGT AAA GTT TTT ACT GAT TAT GTT
ile leu glu gly glu tyr lys gly ile ile asp val ser lys val phe thr asp tyr val
662/221                                 692/231
AAT CAA TCT AAA TTT GAG ACT GGA ACA GCT AAT AGG CTT TTT TTT GAT ACA AGT AAC CAA
asn gln ser lys phe glu thr gly thr ala asn arg leu phe phe asp thr ser asn gln
```

```
722/241                                 752/251
TTA ATA AGC AGA TTG CCT CAA TTT GAG ATT GCA GGA TAT gAA GGA GTA TCC ATT TCA CTT
leu ile ser arg leu pro gln phe glu ile ala gly tyr glu gly val ser ile ser leu
782/261                                 812/271
TTT ACT CAG ATG TGT ACA TTT CAT TTG GGT TTA TTA AAA GAT GGA ATT TTA GCA GGA AGC
phe thr gln met cys thr phe his leu gly leu leu lys asp gly ile leu ala gly ser
842/281                                 872/291
GAT TGG GGA TTT GCT CCT GCA GAT AAA GAC GCT CTT ATT TGC CAA TTC AAT AGA TTT GTC
asp trp gly phe ala pro ala asp lys asp ala leu ile cys gln phe asn arg phe val
902/301                                 932/311
AAT GAA TAT AaT ACt CGA CTG ATG GTA TTG TAC TCA AAA GAA TTT GGA CGG TTA TTA GCA
asn glu tyr asn thr arg leu met val leu tyr ser lys glu phe gly arg leu leu ala
962/321                                 992/331
AAA AAT CTT AAT GAA GCC TTG AAC TTT AGA AAT ATG TGT AGT TTA TAT GTC TTT CCT TTT
lys asn leu asn glu ala leu asn phe arg asn met cys ser leu tyr val phe pro phe
1022/341                                1052/351
TCT GAA GCA TGG TCT TTA TTA AGG TAT GAA GGA ACA AAA TTA GAA AAC ACG CTT TCA TTA
ser glu ala trp ser leu leu arg tyr glu gly thr lys leu glu asn thr leu ser leu
1082/361                                1112/371
TGG AAT TTT GTG GGT GAA AGT ATC AAT AAT ATA TCT CCT AAT GAT TGG AAA GGT GCG CTT
trp asn phe val gly glu ser ile asn asn ile ser pro asn asp trp lys gly ala leu
1142/381                                1172/391
TAT AAA TTG TTA ATG GGA GCA CCT AAT CAA AGA TTA AAC AAT GTT AAG TTT AAT TAT AGT
tyr lys leu leu met gly ala pro asn gln arg leu asn asn val lys phe asn tyr ser
1202/401                                1232/411
TAT TTT TCT GAT ACT CAA GCG ACA ATA CAT CGT GAA AAC ATT CAT GGT GTC CTG CCA ACA
tyr phe ser asp thr gln ala thr ile his arg glu asn ile his gly val leu pro thr
```

FIG. 4B

```
TTAATTATGA AAAGATTTCG TTTATATTAG TAAATTGTTT AAAGAAGAGG GGGCATGTTT    60
TAAATGCAAA ATAACAACTT TAATACCACA GAAATTAATA ATATGATTAA TTTCCCTATG   120
TATAATGGTA GATTAGAACC TTCTCTAGCT CCAGCATTAA TAGCAGTAGC TCCAATTGCT   180
AAATATTTAG CAACAGCTCT TGCTAAATGG GCTGTAAAAC AAGGGTTTGC AAAATTAAAA   240
TCCGAGATAT TCCCCGGTAA TACGCCTGCT ACTATGGATA AGGTTCGTAT TGAGGTACAA   300
ACACTTTTAG ACCAAAGATT ACAAGATGAC AGAGTTAAGA TTTTAGAAGG TGAATACAAA   360
GGAATTATTG ACGTGAGTAA AGTTTTTACT GATTATGTTA ATCAATCTAA ATTTGAGACT   420
GGAACAGCTA ATAGGCTTTT TTTTGATACA AGTAACCAAT TAATAAGCAG ATTGCCTCAA   480
TTTGAGATTG CAGGATATGA AGGAGTATCC ATTTCACTTT TTACTCAGAT GTGTACATTT   540
CATTTGGGTT TATTAAAAGA TGGAATTTTA GCAGGAAGCG ATTGGGGATT TGCTCCTGCA   600
GATAAAGACG CTCTTATTTG CCAATTCAAT AGATTTGTCA ATGAATATAA TACTCGACTG   660
ATGGTATTGT ACTCAAAAGA ATTTGGACGG TTATTAGCAA AAAATCTTAA TGAAGCCTTG   720
AACTTTAGAA ATATGTGTAG TTTATATGTC TTTCCTTTTT CTGAAGCATG GTCTTTATTA   780
```

*FIG. 5A(1)*

```
AGGTATGAAG GAACAAAATT AGAAAACACG CTTTCATTAT GGAATTTTGT GGGTGAAAGT    840
ATCAATAATA TATCTCCTAA TGATTGGAAA GGTGCGCTTT ATAAATTGTT AATGGGAGCA    900
CCTAATCAAA GATTAAACAA TGTTAAGTTT AATTATAGTT ATTTTTCTGA TACTCAAGCG    960
ACAATACATC GTGAAAACAT TCATGGTGTC CTGCCAACAT ATAATGGAGG ACCAACAATT   1020
ACAGGATGGA TAGGGAATGG GCGTTTCAGC GGACTTAGTT TTCCTTGTAG TAATGAATTA   1080
GAAATTACAA AAATAAAACA GGAAATAACT TACAATGATA AAGGGGGAAA TTTCAATTCA   1140
ATAGTTCCTG CTGCTACGCG CAATGAAATT CTAACTGCTA CCGTTCCAAC ATCAGCTGAT   1200
CCATTTTTTA AAACCGCTGA TATTAACTGG AAATATTTCT CTCCGGGTCT TTACTCTGGA   1260
TGGAATATTA AATTTGATGA TACAGTCACT TTAAAAAGTA GAGTACCAAG TATTATACCT   1320
TCAAATATAT TAAAGTATGA TGATTATTAT ATTCGTGCCG TTTCAGCCTG TCCAAAAGGC   1380
GTATCACTTG CATATAACCA TGATTTTTTA ACGTTAACAT ATAATAAATT AGAATATGAT   1440
GCACCTACTA CACAAAATAT CATTGTAGGA TTTTCACCAG ATAATACTAA GAGTTTTTAT   1500
AGGAGCAACT CTCATTATCT AAGTACAACA GATGATGCCT ATGTAATTCC TGCTTTACAA   1560
TTTTCTACAG TCTCAGATAG ATCATTCTTA GAAGATACAC CAGATCAAGC AACAGATGGC   1620
```

FIG. 5A(2)

```
AGTATTAAAT TTACGGATAC TGTTCTTGGG AATGAGGCAA AATATTCTAT TAGACTAAAT    1680
ACTGGATTTA ATACAGCTAC TAGGTATAGA TTAATTATAC GTTTTAAAGC GCCTGCTCGT    1740
TTGGCTGCTG GTATACGTGT ACGTTCTCAA AATTCAGGGA ATAATAAGTT ATTAGGTGGT    1800
ATTCCTGTAG AGGGTAATTC TGGATGGATA GATTATATTA CAGATTCATT TACTTTTGAT    1860
GACCTTGGGA TTACAACTTC AAGTACAAAT GCTTTCTTTA GTATTGATTC AGATGGTGTA    1920
AATGCTTCTC AACAATGGTA TTTGTCTAAA TTAATTTTAG TAAAAGAATC CAGTTTTACG    1980
ACTCAGATTC CATTAAAACC ATACGTTATT GTACGTTGTC CGGATACTTT TTTTGTGAGC    2040
AACAATTCAA GTAGTACGTA CGAACAAGGC TATAACAACA ATTACAACCA GAATTCTAGC    2100
AGTATGTACG ATCAAGGCTA TAACAATAGC TATAATCCAA ACTCTGGTTG TACGTGTAAT    2160
CAAGACTATA ACAATAGCTA TAACCAAAAC TCTGGCTGTA CATGTAACCA AGGGTATAAC    2220
AATAACTATC CTAAATAAGA AAACAATGAA AAAGCATTCC CCTCTCACAA GGAATGCTTT    2280
TTTGTCTGCC CTATTTTACG CATATATAAA ACCCATTGGT AATTGCATAC TATGCATACT    2340
CTATAAAACC GTTCCATCCT ACCCCTGTTA TGAAGTGACC TTTGTCAATA GTTTTTCAAC    2400
CATAATATTT TTTCTTGATG GCATACAAAA GCTT                                2434
```

*FIG. 5A(3)*

FIG. 5B(1)

Met Gln Asn Asn Asn Phe Asn Thr Thr Glu Ile Asn Asn Met Ile Asn
1 5 10 15

Phe Pro Met Tyr Asn Gly Arg Leu Glu Pro Ser Leu Ala Pro Ala Leu
20 25 30

Ile Ala Val Ala Pro Ile Ala Lys Tyr Leu Ala Thr Ala Leu Ala Lys
35 40 45

Trp Ala Val Lys Gln Gly Phe Ala Lys Leu Lys Ser Glu Ile Phe Pro
50 55 60

Gly Asn Thr Pro Ala Thr Met Asp Lys Val Arg Ile Glu Val Gln Thr
65 70 75 80

Leu Leu Asp Gln Arg Leu Gln Asp Asp Arg Val Lys Ile Leu Glu Gly
85 90 95

Glu Tyr Lys Gly Ile Ile Asp Val Ser Lys Val Phe Thr Asp Tyr Val
100 105 110

Asn Gln Ser Lys Phe Glu Thr Gly Thr Ala Asn Arg Leu Phe Phe Asp
115 120 125

Thr Ser Asn Gln Leu Ile Ser Arg Leu Pro Gln Phe Glu Ile Ala Gly
130 135 140

Tyr Glu Gly Val Ser Ile Ser Leu Phe Thr Gln Met Cys Thr Phe His
145 150 155 160

Leu Gly Leu Leu Lys Asp Gly Ile Leu Ala Gly Ser Asp Trp Gly Phe
165 170 175

Ala Pro Ala Asp Lys Asp Ala Leu Ile Cys Gln Phe Asn Arg Phe Val
180 185 190

Asn Glu Tyr Asn Thr Arg Leu Met Val Leu Tyr Ser Lys Glu Phe Gly
195 200 205

FIG. 5B(2)

Arg Leu Leu Ala Lys Asn Leu Asn Glu Ala Leu Asn Phe Arg Asn Met
210 215 220

Cys Ser Leu Tyr Val Phe Pro Phe Ser Glu Ala Trp Ser Leu Leu Arg
225 230 235 240

Tyr Glu Gly Thr Lys Leu Glu Asn Thr Leu Ser Leu Trp Asn Phe Val
245 250 255

Gly Glu Ser Ile Asn Asn Ile Ser Pro Asn Asp Trp Lys Gly Ala Leu
260 265 270

Tyr Lys Leu Leu Met Gly Ala Pro Asn Gln Arg Leu Asn Asn Val Lys
275 280 285

Phe Asn Tyr Ser Tyr Phe Ser Asp Thr Gln Ala Thr Ile His Arg Glu
290 295 300

Asn Ile His Gly Val Leu Pro Thr Tyr Asn Gly Gly Pro Thr Ile Thr
305 310 315 320

Gly Trp Ile Gly Asn Gly Arg Phe Ser Gly Leu Ser Phe Pro Cys Ser
325 330 335

Asn Glu Leu Glu Ile Thr Lys Ile Lys Gln Glu Ile Thr Tyr Asn Asp
340 345 350

Lys Gly Gly Asn Phe Asn Ser Ile Val Pro Ala Ala Thr Arg Asn Glu
355 360 365

Ile Leu Thr Ala Thr Val Pro Thr Ser Ala Asp Pro Phe Phe Lys Thr
370 375 380

Ala Asp Ile Asn Trp Lys Tyr Phe Ser Pro Gly Leu Tyr Ser Gly Trp
385 390 395 400

Asn Ile Lys Phe Asp Asp Thr Val Thr Leu Lys Ser Arg Val Pro Ser
405 410 415

FIG. 5B(3)

Ile Ile Pro Ser Asn Ile Leu Lys Tyr Asp Asp Tyr Tyr Ile Arg Ala
420 425 430

Val Ser Ala Cys Pro Lys Gly Val Ser Leu Ala Tyr Asn His Asp Phe
435 440 445

Leu Thr Leu Thr Tyr Asn Lys Leu Glu Tyr Asp Ala Pro Thr Thr Gln
450 455 460

Asn Ile Ile Val Gly Phe Ser Pro Asp Asn Thr Lys Ser Phe Tyr Arg
465 470 475 480

Ser Asn Ser His Tyr Leu Ser Thr Thr Asp Asp Ala Tyr Val Ile Pro
485 490 495

Ala Leu Gln Phe Ser Thr Val Ser Asp Arg Ser Phe Leu Glu Asp Thr
500 505 510

Pro Asp Gln Ala Thr Asp Gly Ser Ile Lys Phe Thr Asp Thr Val Leu
515 520 525

Gly Asn Glu Ala Lys Tyr Ser Ile Arg Leu Asn Thr Gly Phe Asn Thr
530 535 540

Ala Thr Arg Tyr Arg Leu Ile Ile Arg Phe Lys Ala Pro Ala Arg Leu
545 550 555 560

Ala Ala Gly Ile Arg Val Arg Ser Gln Asn Ser Gly Asn Asn Lys Leu
565 570 575

Leu Gly Gly Ile Pro Val Glu Gly Asn Ser Gly Trp Ile Asp Tyr Ile
580 585 590

Thr Asp Ser Phe Thr Phe Asp Asp Leu Gly Ile Thr Thr Ser Ser Thr
595 600 605

Asn Ala Phe Phe Ser Ile Asp Ser Asp Gly Val Asn Ala Ser Gln Gln
610 615 620

FIG. 5B(4)

Trp Tyr Leu Ser Lys Leu Ile Leu Val Lys Glu Ser Ser Phe Thr Thr
625 630 635 640

Gln Ile Pro Leu Lys Pro Tyr Val Ile Val Arg Cys Pro Asp Thr Phe
645 650 655

Phe Val Ser Asn Asn Ser Ser Ser Thr Tyr Glu Gln Gly Tyr Asn Asn
660 665 670

Asn Tyr Asn Gln Asn Ser Ser Ser Met Tyr Asp Gln Gly Tyr Asn Asn
675 680 685

Ser Tyr Asn Pro Asn Ser Gly Cys Thr Cys Asn Gln Asp Tyr Asn Asn
690 695 700

Ser Tyr Asn Gln Asn Ser Gly Cys Thr Cys Asn Gln Gly Tyr Asn Asn
705 710 715 720

Asn Tyr Pro Lys

```
ACTGTTTCCA GTGAAGTATT GTCCCCATCC TACCTTGCCA AAATATCTCA TACGTATCAT     60
ACGTTAATGG TTACCCAAAA TATATACGCA TTTTATCCCG TCTGTTTTTT CGTAAGGAAC    120
ACTCTCCCCT TACGAAAAAG TAACAAAAGA ATAAATCCTA TCAATAACAA TATGGGAACC    180
AATGTACATG TCGGTCTCAA AACCAATATC GATAACAATA TCAGAACTAA TGTGCATGTT    240
GGTCTCAAAC CTAATATCGA TAACAATATC GGAACTAGCA TGTATGACGA TCTTAAGACC    300
AACATTAACA ACAATATCGG AACAAGCATG CATGATGAAC TTAACAACGA GTGTTTTTTT    360
CATAGGCCTG TTGCATGTTA TTGCATACCA AAATTACCTT AGACTCAGCA TTTTGACCTA    420
AGAAAATGAT TTTAATTAAA TCTGTTTATG GTAACAACTC TTCGTAAATG TGGTAGACTT    480
AGTTATGATT TCTTTCGTAA ACATGAACTT CAACATTAGG GTTCCAGTAG TTTTCATTTA    540
CTTAGACATT ATATTAGATA GGTAGGTCTT AATGGGAGAT GTCCTTATGG TGGATTATTG    600
AATAATAAGG GACTTAAAAC TCTTGCATGT GCATATGGTC GTCGGTTTGC TCGTCCGCGA    660
AATTTTGCAT ATTAATTAGA TATGGATCAT CGACATAATT TAGGTCATAA ATCAGATTAT    720
CTTATAAAAC GGAGTAAGGG TTCTTGTCAT AGGCATTTAA ATTATGACGG TAGACAACGA    780
ACTAGACCAC ATAGAAGATT CTTACTAGAT AGACTCTGAC ATCTTTTAAC ATTTCGTCCT    840
TAATGTATCC GTAGTAGACA ACATGAATCT ATTACTCTCA ACGAGGATAT TTTTGAGAAT    900
CATAATAGAC CACTTTTAGG ATGTTACTAT AAAACACATC ATCCACGTAG TATAAGATTA    960
AATAATATAC AATTGCAATT TTTTAGTACC AATATACGTT CACTATGCGG AAAACCTGTC   1020
CGACTTTGCC GTGCTTATAT TATTAGTAGT ATGAAATTAT ATAAACTTCC ATATTATGAA   1080
CCATGAGATG AAAAATTTCA CTGACATAGT AGTTTAAATT ATAAGGTAGG TCTCATTTCT   1140
GGGCCTCTCT TTATAAAGGT CAATTATAGT CGCCAAAATT TTTTACCTAG TCGACTACAA   1200
CCTTGCCATC GTCAATCTTA AAGTAACGCG CATCGTCGTC CTTGATAACT TAACTTTAAA   1260
GGGGGAAATA GTAACATTCA ATAAAGGACA AAATAAAAAC ATTAAAGATT AAGTAATGAT   1320
GTTCCTTTTG ATTCAGGCGA CTTTGCGGGT AAGGGATAGG TAGGACATTA ACAACCAGGA   1380
GGTAATATAC AACCGTCCTG TGGTACTTAC AAAAGTGCTA CATAACAGCG AACTCATAGT   1440
CTTTTTATTG ATATTAATTT GAATTGTAAC AAATTAGAAA CTAATCCACG AGGGTAATTG   1500
TTAAATATTT CGCGTGGAAA GGTTAGTAAT CCTCTATATA ATAACTATGA AAGTGGGTGT   1560
TTTAAGGTAT TACTTTCGCA CAAAAGATTA AAACAAGGAA GTATGGAATT ATTTCTGGTA   1620
```

*FIG. 6A(1)*

```
CGAAGTCTTT TTCCTTTCTG TATATTTGAT GTGTATAAAG ATTTCAAGTT CCGAAGTAAT 1680
TCTAAAAAAC GATTATTGGC AGGTTTAAGA AAACTCATGT TATGGTAGTC AGCTCATAAT 1740
ATAAGTAACT GTTTAGATAA CTTAACCGTT TATTCTCGCA GAAATAGACG TCCTCGTTTA 1800
GGGGTTAGCG AAGGACGATT TTAAGGTAGA AAATTATTTG GGTTTACTTT ACATGTGTAG 1860
ACTCATTTTT CACTTTACCT ATGAGGAAGT ATAGGACGTT AGAGTTTAAC TCCGTTAGAC 1920
GAATAATTAA CCAATGAACA TAGTTTTTTT TCGGATAATC GACAAGGTCA GAGTTTAAAT 1980
CTAACTAATT GTATTAGTCA TTTTTGAAAT GAGTGCAGTT ATTAAGGAAA CATAAGTGGA 2040
AGATTTTAGA ATTGAGACAG TAGAACATTA GAAACCAGAT TTTCACAAAC ATGGAGTTAT 2100
GCTTGGAATA GGTATCATCG TCCGCATAAT GGCCCCTTAT AGAGCCTAAA ATTAAAACGT 2160
TTGGGAACAA AATGTCGGGT AAATCGTTCT CGACAACGAT TTATAAATCG TTAACCTCGA 2220
TGACGATAAT TACGACCTCG ATCTCTTCCA AGATTAGATG GTAATATGTA TCCCTTTAAT 2280
TAGTATAATA ATTAAAGACA CCATAATTTC AACAATAAAA CGTAAATTTT GTACGGGGGA 2340
GAAGAAATTT GTTAAATGAT TATATTTGCT TTAGAAAAGT ATTAATTGAA AAAACAAAAG 2400
GTTATCATAT GGATAAAAAT ATGTCAATAT TAATAAGAAC AAAATTTCCA TGTATATAAA 2460
TATTTAGTAT CCCACGTAAA TTAAAGGTAA TAAGTCCTAA GACCTGACTT TATTTTTACT 2520
CTTAAGTGTA GATTAATTAC CTTGAAACAC TAAAAGAAGA CTGTACATTA GTATACTACT 2580
AAGACCAACG TTTATACTAA AGAAAAGTTT TAATAGTATT AGTCATAAGT GCATTATTAG 2640
GAGTGTAGGA AAAGATAAAA GTGAAGATAA AGCAGTTAGC AATCAAATAA AGGACAAAAA 2700
AATTAAACAA TAGAAAAACG TGGTCTTTGT TTTTTTGGAC GTATACGCCC TAAACATATG 2760
TGAAGTTTCA GTGTGGACCA GTTAGGAAAA AATGCGTCTC ATAATGGTTT CCCAAGACAA 2820
CGTTTCAAGA AAAGTCGACC AATGTTAAAT CTTTTTCGAC ACTCCTCTTA ACGTTTACCC 2880
TATAAAATTT CCTTTTGTTA AGTTCTTTCT ATAATAAAAA CATCGGCAAC CGATGATAAC 2940
AGCAAAAAGA AATTCGATAG CACTACATAG ACTTTAAGAC TTTCTTGCTC CGCAAAGGCA 3000
AGTGGGTTGT TGTTAGTACG CTACCCACGT ACTTATACCG TTAGACTAGA TAGTTTAGAC 3060
CTTTTTCTTT TTGTGTTGTA GAGTTAGCAG TACCGTAAAT CTACTTTGCA TATAGTTTCA 3120
GTTTCCGCTT ACCACGATAG ATATAGCACG ATAACTATCA CTACCTGTAT GCGAACTAAA 3180
AGTTGAAGCA GTTTGTGCGC TAGTAGTTCG GCGAATATAC AAATACTTTG CTAATCACTT 3240
```

FIG. 6A(2)

*FIG. 6B*

```
TTGAAAACCT CTTGGTTTCC AAGAATAATG TCTATTCCGA GGACGTGACG AAACACGCAA   3300
ATTTTTTGAT TTTTTCTTGC CACACATACA CGTATGTTTT GTAACATGCC AATTTGTAGA   3360
ATTATTGGAC TAACTTGTTC TGGTGGCTGT ACATTTTGCT GCAAAACGGT TTAGAAGACC   3420
TAAGGTTTTA TAGGCGGTAC GAAGTGCATG GTATTTTCCC TAACTTTGCT AAGTCCGGAA   3480
TATATTTGTC TCTGCTTCAA ACTTAGTCTG AGGCAGAAAA GACGCATGTT ACTTGACGTT   3540
GTTAATGATC GCTGACGAAT TGATAAAGAG TAGTAAAAGG TTCCGCAAAT ATGAAAAAAG   3600
TTTGAAACGT TGTCTTGGAG TACGGAATAT ATAAAATGAA GTCTTTCTAA TTGGCAATGA   3660
ACTCTTCCTA GTGAA                                                    3675
```

```
Jeg80  MMQNNNFNTTEINNMINFPMYNGRLEPSLAPALIAVAPIAKYLATALAKWAVKQGFAKLKS  60
                          :       ::                 ::      :   :
CryIVD MMEDSSLDTLSIVNETDFPLYNNYTEPTIAPALIAVAPIAQYLATAIGKWAAKAAFSKVLS  60

Jeg80  EIFPGNTPATMDKVRIEVQTLLDQRLQDDRVKILEGEYKGIIDVSKVFTDYVNQSKFETG 120
                  :          :  :         :   :   :       :       :
CryIVD LIFPGSQPATMEKVRTEVETLINQKLSQDRVNILNAEYRGIIEVSDVFDAYIKQPGFTPA 120

Jeg80  TANRLFFDTSNQLISRLPQFEIAGYEGVSISLFTQMCTFHLGLLKDGILAGSDWGFAPAD 180

CryIVD TAKGYFLNLSGAIIQRLPQFEVQTYEGVSIALFTQMCTLHLTLLKDGILAGSAWGFTQAD 180
                                 ←         Block 1          →

Jeg80  KDALICQFNRFVNEYNTRLMVLYSKEFGRLLAKNLNEALNFRNMCSLYVFPFSEAWSLLR 240
                    :        ::            ::                    :
CryIVD VDSFIKLFNQKVLDYRTRLMRMYTEEFGRLCKVSLKDGLTFRNMCNLYVFPFAEAWSLMR 240

Jeg80  YEGTKLENTLSLWNFVGESINNISPNDWKGALYKLLMGAPNQRLNNVKFNYSYFSDTQAT 300
                :     :      :   :    :                    :  :
CryIVD YEGLKLQSSLSLWDYVGVSI-PVNYNEWGGLVYKLLMGEVNQRLTTVKFNYSFTNEPADI 299
```

*FIG. 7A(1)*

```
Jeg80  IHRENIHGVLPTYNGGPTITGWIGNGRFSGLSFPCSNELEITKIKQEITYNDKGGNFNSI 360
                         :                        ::     :
CryIVD PARENIRGVHPIYDPSSGLTGWIGNGRTNNFNFADNNGNEIMEVRTQTFYQNPNN--EPI 357
                                                       ↑↑          ↑

Jeg80  VPAATRNEILTATVPTSADPFFKTADINWKY---FSPGLYSGWNIKFDDTVTLKSRVPSI 417
                                     :     ::                    :
CryIVD APRDIINQILTA--PAPADLFFKNADINVKFTQWFQSTLY-GWNIKLGTQTVLSSR-TGT 413

Jeg80  IPSNILKYDDYYIRAVSACPKGVSLAYNHDFLTLTYNKLEYDAPTTQNIIVGFSPDNTKS 477
                      :    :                ::
CryIVD IPPNYLAYDGYYIRAISACPRGVSLAYNHDLTTLTYNRIEYDSPTTENIIVGFAPDNTKD 473

Jeg80  FYRSNSHYLSTTDDAYVIPALQFSTVSDRSFLEDTPDQATDGSIKFTDTVLGNEAKYSIR 537
                                                         :
CryIVD FYSKKSHYLSETNDSYVIPALQFAEVSDRSFLEDTPDQATDGSIKFARTFISNEAKYSIR 533

Jeg80  LNTGFNTATRYRLIIRFKAPARLAAGIRVRSQNSGNNKLLGGIPVEGNSGWIDYITDSFT 597
                  :     :                   ::        :    : ::
CryIVD LNTGFNTATRYKLIIRVRVPYRLPAGIRVQSQNSGNNRMLGSFTANANPEWVDFVTDAFT 593
                 ←  Block 4?→
```

*FIG. 7A(2)*

FIG. 7B

```
Jeg80  FDDLGITTSSTNAFFSIDSDGVNASQQWYLSKLILVKESSFTTQIPLKPYVIVRCPDTFF 657
                             :
CryIVD FNDLGITTSSTNALFSISSDSLNSGEEWYLSQLFLVKESAFTTQINPLLK         643

Jeg80  VSNNSSSTYEQGYNNNYNQNSSSMYDQGYNNSYNPNSGCTCNQDYNNSYNQNSGCTCNQG 717

Jeg80  YNNNYPK 724
```

POLYPEPTIDES HAVING A TOXIC ACTIVITY AGAINST INSECTS OF THE DIPTERAE FAMILY

The biological control of insects of the Diptera family, which comprises for example the mosquitoes and the simuliids, vectors of tropical diseases, is principally conducted with the aid of the bacteria *Bacillus thuringiensis* ser. *israelensis* (Bti) of the H14 serotype or with the aid of *Bacillus sphaericus*. During sporulation these two bacteria synthesize proteins assembled in the form of crystals, which are toxic for the insect larvae on ingestion. The crystals of *B. thuringiensis* ser. *israelensis* are composed of 4 major polypeptides CryIVA (125 kDa), CryIV B (135 kDa), CryIV D (68 kDa) and Cyt A (28 kDa) (Höfte H et al., 1989 Microbiol. Rev. 53:242–255). The crystals of *B. sphaericus* are constituted of 2 polypeptides of 51 and 42 kDa. These proteins have different specificities and each of them contributes to the total toxicity, acting if necessary in synergy. With the objective of neutralizing the possible appearance of insects resistant to the Bti toxins, the search for novel strains exhibiting an activity against mosquitoes was undertaken.

The *B. thuringiensis* strains active against mosquitoes may be classed in four groups depending on their larvicidal activity, the protein composition of their crystals and the presence of genes related to those of the *B. thuringiensis* ser. *israelensis* strain:

(1) group 1 contains the six strains of *B. thuringiensis* designated respectively as *morrisoni* PG14 (H8a8b), *canadensis* 11S2-1 (H5a5c), *thompsoni* B175 (H12), *malaysiensis* IMR81.1 (H36), K6 (autoagglutinating), and B51 (autoagglutinating) which have a similar larvicidal activity and polypeptides of the crystal similar to those of *B. thuringiensis* ser. *israelensis*, (2) group 2 includes the two *B. thuringiensis* strains *medellin* 163-131 (H30) and *jegathesan* 367 (H28a28c) which are almost as toxic as the *B. thuringiensis* ser. *israelensis* strain but which produce different polypeptides, (3) group 3 comprises the strain *darmstadiensis* 73E10-2 (H10a10b) which synthesizes polypeptides different from those found in the crystals of *Bacillus thuringiensis* ser. *israelensis* but which is active on only one species of mosquito, and (4) group 4 which includes the two strains *fukuokaensis* (H3a3d3e) and Kyushuensis 74 F6-18 (H11a11c) which are only weakly toxic.

Given the low toxicity of the strains of groups 3 and 4, these strains have not been studied in detail.

Of all the strains isolated the *Bacillus thuringiensis* ser *jegathesan* 367 (Btjeg) strain, of the H28a 28c serotype, seems interesting both from the point of view of its activity and from the polypeptide composition of its crystals. Like Bti this bacterium produces crystals during sporulation which are toxic to mosquito larvae when ingested. This strain was isolated in Malaysia by L. LEE and identified as belonging to a new subtype.

The crystals of *B. thuringiensis* ser. *jegathesan* contain 7 major polypeptides having a molecular weight of 80, 72–70, 65, 37, 26 and 16 kDa, respectively. The 37 kDa protein is immunologically related to a constituent of the crystal of *B. thuringiensis* ser. *israelensis* whereas the other proteins only give weak or variable cross-reactions. No gene related to those of *B. thuringiensis* ser. *israelensis* was detected in this strain, indicating that the proteins of the crystal might be encoded in a new class of toxin genes.

The inventors have identified within the total DNA of a Btjeg 367 strain, sequences coding for polypeptides capable of inducing and/or contributing to the toxic activity of the strain against insects of the Diptera family in particular.

Hence the object of the invention is nucleotide sequences coding for polypeptides with toxic activity against insects. Target insects are for example insects of the Diptera family, in particular mosquitoes or simuliids and especially the larvae of these insects. However, it is not excluded that the polypeptides obtained from the sequences of the invention may exhibit an activity against insects of other families.

The application also concerns polypeptides having a larvicidal activity against insects, or polypeptides capable of contributing to such a toxic activity, if necessary by acting in synergy with polypeptides determining this activity.

Thus the polypeptides of the invention are capable either of inducing the toxic activity or of enhancing the level of toxicity against a given target.

Also included in the context of the invention are larvicidal compositions containing as active ingredient the polypeptides of the invention or recombinant organisms capable of expressing such polypeptides, if necessary combined with other constituents, for example, other polypeptides or recombinant cells capable of increasing the desired toxic activity, if necessary derived from other organisms, for example *Bacillus thuringiensis, Bacillus sphaericus, Clostridium bifermentans.*

A first group of sequences contains a first nucleotide sequence characterized in that it corresponds to the HindIII fragment of about 4.3 kb which can be obtained from the plasmid pJEG80.1 deposited with the CNCM (Collection Nationale De Cultures De Microoraganismes, Institut Pasteur, 25 rue du docteur Roux, 75724 Paris Cedex 15, France) under the number 1-1469 on Aug. 23, 1994 or which can hybridize with this plasmid under stringent conditions.

Figure 3:
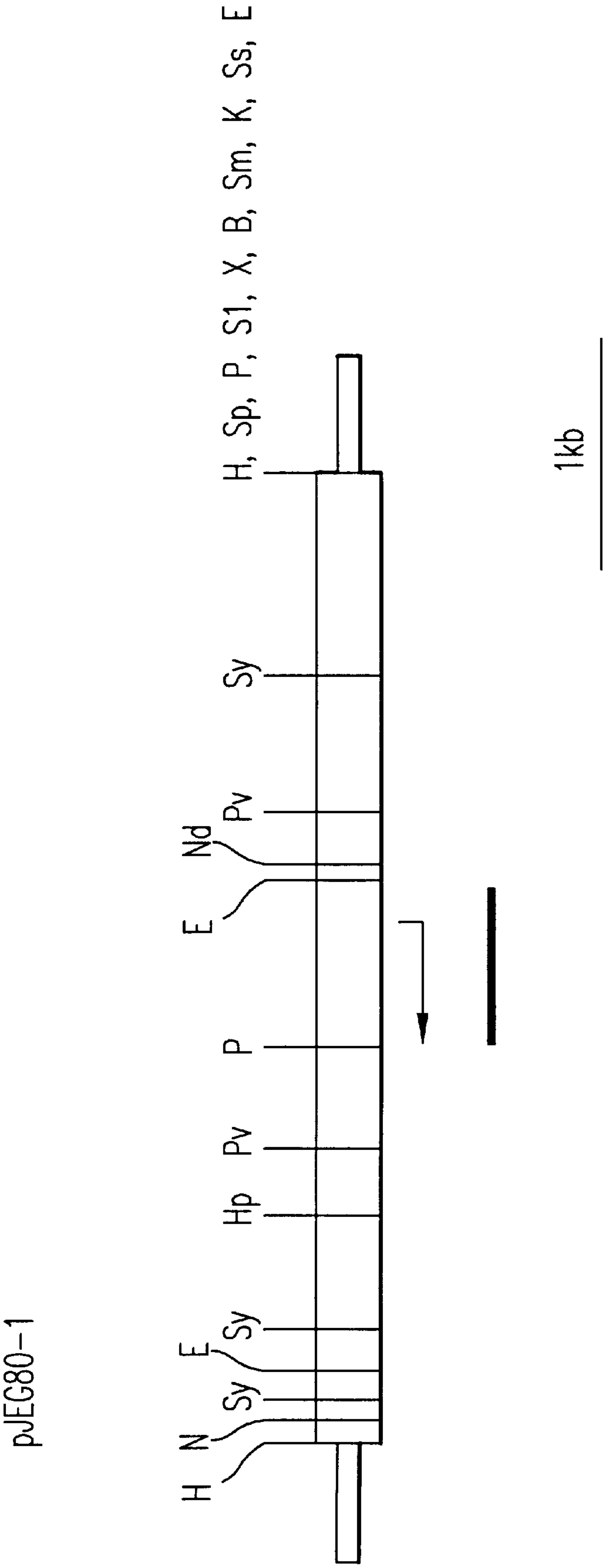

The restriction map of the Btjeg sequence contained in the recombinant plasmid pJEG80.1. is shown in FIG. 3 and shows the position of the start of the jeg80 gene as well as the sense in which it is transcribed.

According to a particular embodiment of the invention, a nucleotide sequence of this first group is included in the HindIII fragment of about 4.3 kb shown in FIG. 3, which can be isolated from the plasmid pJEG80.1 deposited with the CNCM. An interesting fragment is for example the HindIII-NdeI fragment of about 2.2 kb. This fragment contains the origin of the jeg80 gene.

According to another particular embodiment of the invention, the nucleotide sequence corresponding to the preceding definition is additionally characterized in that it includes the nucleotide sequence shown in FIG. 4 (SEQ ID NO:1,2).

The invention also relates to the jeg80 gene shown in FIG. 5A, the coding sequence of which is included between the nucleotides 64 and 2238 (SEQ ID NO:3).

The invention also relates to the non-coding sequence upstream from the coding sequence of the jeg80 gene, which contains the sequences regulating the expression of the gene. In particular, the invention relates to the fragment included between the nucleotides 1 and 124 of the sequence shown in FIG. 4 (SEQ ID NO:1).

The invention also relates to nucleotide sequences modified with respect to the sequences previously defined, for example by deletion, addition or substitution of nucleotides, characterized in that they hybridize under stringent conditions with one of the sequences previously defined, and in that they code in addition for a polypeptide having a toxic activity against insects of the Diptera family or which contribute to this activity.

By polypeptides according to the present description is meant peptides, polypeptides or proteins or any amino acid sequence having the required properties.

The observed toxic activity against insects of the Diptera family must in no case be considered as limiting for the definition of the sequences of the invention. On the contrary, this reference to the Diptera only constitutes a criterion for assessing the value of a given sequence, although in fact, as regards the toxic activity, the target insects may belong to other families.

The toxic activity assessed with respect to insects of the Diptera family may for example be tested in mosquitoes or simuliids or in the larvae of these insects.

The toxic activity of the expression product of a nucleotide sequence of the invention may be assessed by measuring the lethal dose necessary to kill 50% of a sample of insect larvae tested ($LC_{50}$), when the test is performed in 150 ml of water with 25 larvae per beaker, these larvae being in the L4 stage in the case of *Aedes aegypti* and *Culex pipiens* and stage L3 in the case of *Anopheles stephensi*. Variable quantities of toxins are added to the beakers. The Culex and Anopheles larvae are fed on beer yeast at a concentration of 50 mg/l. The test is read at 24 h and 48 h.

A nucleotide sequence coding for a polypeptide having a toxic activity against insects of the Diptera family according to the invention is for example a sequence coding for a polypeptide having a molecular weight of about 80 kDa.

The object of the invention is also any fragment derived from a nucleotide sequence corresponding to one of the preceding criteria and hybridizing under stringent conditions with one of these sequences, this fragment having at least 9 nucleotides. Such fragments are designed in particular to be used as hybridization probes or as oligonucleotide primers for performing chain amplification reactions such as the PCR. As an example, an interesting nucleotide sequence is the j80 sequence corresponding to the following chain (SEQ ID NO:8):

AATAATATGATIAATTTTCCIATGTA (26-mer)

The object of the present application is also a second group of nucleotide sequences, a representative of which for example is a nucleotide sequence characterized in that it codes for a polypeptide which, in combination with a polypeptide encoded in a nucleotide sequence of the first group presented above is capable of contributing to the toxic activity of this latter against insects of the Diptera family, this sequence hybridizing in addition with the oligonucleotide j66 which has the following sequence (SEQ ID NO:9):

ATGCATTATTATGGIAATIGIAATGA

The definition of this nucleotide sequence with respect to its capacity to contribute to the toxic activity of the polypeptide encoded in one of the sequences of the first group does not excluded the possibility that this nucleotide sequence codes for a peptide having its own intrinsic toxic activity against insects of the Diptera family.

The value of this second group of nucleotide sequences may for example result from the fact that its association with polypeptides encoded in the first group of sequences previously defined may lead to a synergy such that the toxic activity of the combination of polypeptides is higher than the sum of the individual activities of each of the polypeptides of the combination. A particular nucleotide sequence of this second group codes for a polypeptide of about 66 kDa.

A third group of nucleotide sequences is characterized in that they code for polypeptides which, in combination with a polypeptide encoded in a nucleotide sequence of the first group or second group, are capable of contributing to the toxic activity of these polypeptides against insects of the Diptera family, these nucleotide sequences being in addition characterized in that they hybridize with the oligonucleotide j37 which has the following sequence (SEQ ID NO:10):

AATATIGAAATIGCIACAAGAGATTA

A preferred nucleotide sequence of this third group is characterized in that it codes for a polypeptide of about 37 kDA.

The object of the invention is a fourth group of nucleotide sequences coding for a polypeptide which, in combination with at least one of the preceding, is also capable of contributing to the toxic activity observed against insects of the Diptera family, the sequences of this fourth group coding for a polypeptide having a molecular weight of about 70 kDa or producing an immunological reaction with this peptide.

The hybridization conditions with the oligonucleotides are the stringent hybridization conditions described in the kit "ECL 3 oligo-labelling detection kit" from Amersham, the hybridization temperature being 42° C. and the second washing after hybridization being made in 1 x SSC - 0.1% SDS.

The object of the invention also includes the sequences flanking that of the jeg80 gene, corresponding to the ISjeg between the nucleotides 2812 and 3618 of the sequence of FIG. 6 (SEQ ID NO:5) and the intergenic region between the nucleotides 1604 and 284 of FIG. 6.

The object of the invention also includes a cloning or expression vector, characterized in that it comprises a nucleotide sequence corresponding to the previously given definitions.

A particularly preferred vector is the plasmid pJEG80.1 deposited with the CNCM on Aug. 23, 1994 under No. I-1469.

The object of the present application is also polypeptides characterized in that they constitute the expression product in a recombinant cell of at least one of the nucleotide sequences of the first, second, third or fourth groups such as defined in the previous pages.

In particular, the invention relates to the polypeptide Jeg80 encoded in the jeg80 gene shown in FIG. 5A.

Preferred polypeptides are for example the polypeptide of about 80 kDa represented by the amino acid sequence shown in FIG. 4, or the polypeptide of about 80 kDa corresponding to the amino acid sequence shown in FIG. 5B (SEQ ID NO:4), or any fragment of this polypeptide reacting with antibodies directed against the 80 kDa protein corresponding to the sequence shown in FIG. 5B and/or exhibiting a toxic activity against insect larvae of the Diptera family.

The polypeptides of the invention may be used alone or in combination. The combinations (or mixtures) may consist of different polypeptides of the groups I, II, III or IV such as were described above and/or a mixture of one or more of these polypeptides with other polypeptides derived from different organisms and in particular strains of Bti, *B. sphaericus* or *C. bifermentans* also having a toxic activity against insects.

Also included in the context of the present application are recombinant cells modified by a nucleotide sequence such as defined in the preceding pages or by a vector containing one of these sequences.

These recombinant host cells are prokaryotic or eukaryotic cells and they may be for example bacterial cells, for example strains of *Bacillus thuringiensis* strain Bti or *Bacillus sphaericus*, even *Clostridium bifermantans*.

As regards *B. thuringiensis*, reference should be made to the publication of Lereclus D. et al. (1989), FEMS Microbiology Letters 60, 211–218, in which the procedure for the transformation of *B. thuringiensis* (by the introduction of the toxin genes into Bt) is described.

As regards *B. sphaericus*, reference should be made for example to the publication of Taylor L. D. et al. (1990) FEMS Microbiology Letters 66, 125–128.

Another cell according to the invention may be a eukaryotic cell, for example a plant cell.

The recombinant cells may be used to produce the polypeptides of the invention, but may also be used in toxic compositions against insects.

The object of the application also includes polyclonal antibodies directed against one of the polypeptides defined above, or even a polyclonal serum directed against a mixture of several of them.

Other characteristics and advantages of the invention will become apparent in the examples and the figures which follow.

FIG. 1A Polypeptide composition of the crystals of the strain Btjeg. The crystals of the natural strains Bti and Btjeg, and the recombinant strain 407 (pJEG80.1) were purified and loaded on to a SDS-10% polyacrylamide gel. After electrophoresis, the gel was stained with Coomassie blue. The molecular mass (in kDa) of protein standards is shown on the right. The molecular masses of the Btjeg proteins are indicated on the left. Lane: 1, Bti; 2, Btjeg; 3, 407 (pJEG80.1).

Figure 1B:
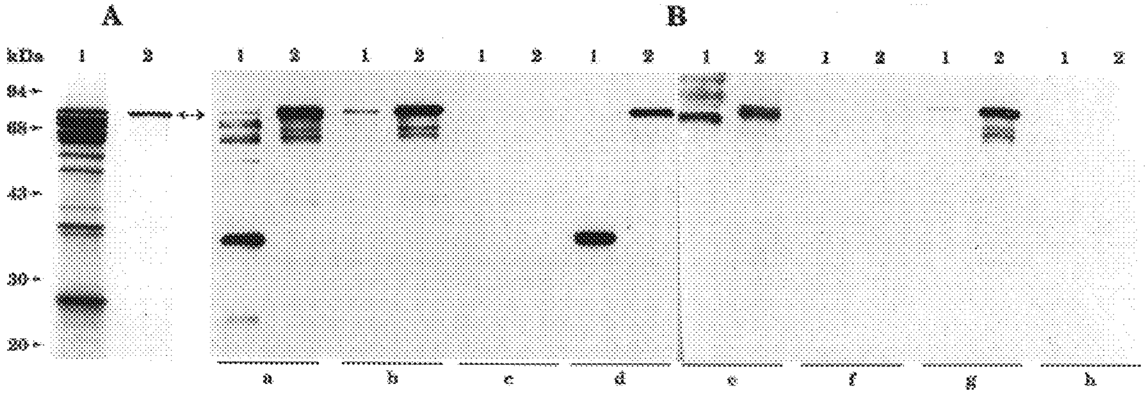

FIG. 1B Analysis of the proteins contained in the inclusions produced by the strain 407 (pJEG80.1). A: Purified inclusions corresponding to 10 μg of proteins subjected to electrophoresis and stained with Coomassie Blue. B: Purified inclusions corresponding to 1 μg of proteins subjected to electrophoresis and transferred to a nitrocellulose filter. The filter was incubated with the antiserum (diluted 5,000 fold) against the total crystals of Bt ser. *jegathesan* (a), ser. *medellin* (b), ser. *darmstadiensis* (c), ser. *israelensis* (d) or against the solubilized purified inclusions composed of CryIVA (e), CryIVB (f), CryIVD (g) or CytA (h). The immunoreactive polypeptides were revealed with a second antibody conjugated to peroxidase (diluted 20,000 fold). The arrows between A and B give the position of Jeg80. The numbers on the left give the molecular weights (kDa) of the protein standards; line 1: the purified inclusions of the Btjeg 407 strain; line 2: the purified inclusions of the strain 407 (pJEG80.1).

Figure 2:
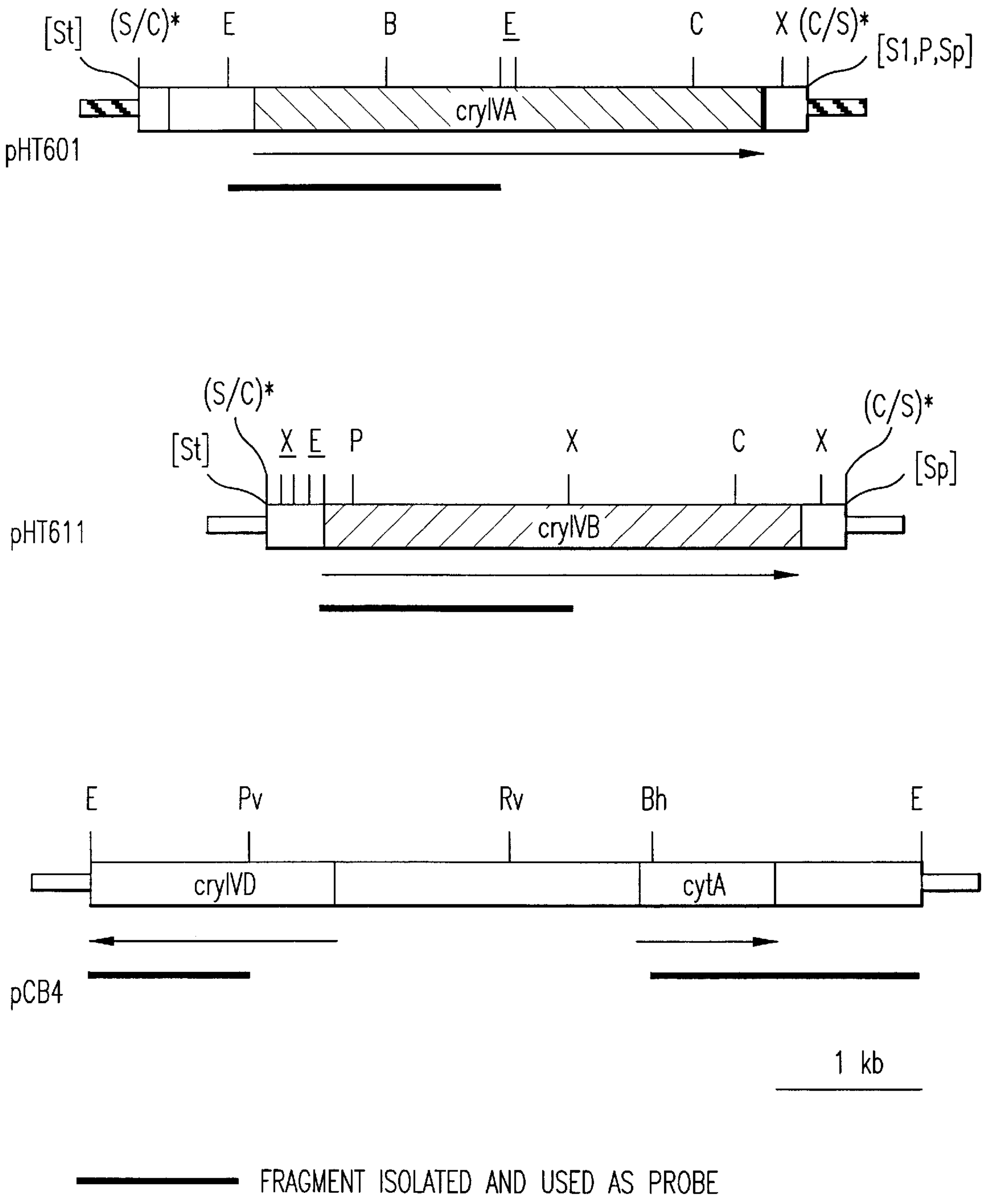

FIG. 2 Probes used to determine the presence of the Bti toxin genes in Btjeg.

FIG. 3 Restriction map of the pJEG80.1 plasmid Vector pHT315 Fragment hybridizing with the oligonucleotide j80 Start of the jeg80 gene and sense of transcription DNA fragment of Btjeg cloned into the HindIII site of the plasmid pHT315 Polylinker restriction site No restriction site was found for the following enzymes: BamHI, BglII, ClaI, EcoRV, KpnI, NcoI, SacI, SacII, SmaI, SphI, XbaI and XhoI H=HindIII; E=EcoRI; K=KpnI; Hp=HpaI; B=BamHI; N=NsiI; Nd=NdeI; P=PstI; Pv=PvuII; Sm=SmaI; Sp=SphI; Ss=SstI; SI=SalI; Sy=StyI; X=XbaI.

FIG. 4 Nucleotide sequence of a part of the jeg80 gene and amino acid sequence corresponding to the coding sequence (SEQ ID NO:1,2): the sequence in the box represents the amino acid sequence determined by microsequencing.

FIG. 5A: jeg80 gene. The potential ribosomal binding site is underlined. The start and stop codons of translation are indicated. The inverted repeat sequences are marked by arrows. B: Amino acid sequence of the JEG80 protein (SEQ ID NO:4).

FIG. 6 Nucleotide sequence of the jeg80 gene (coding sequence included between the nucleotides 64 and 2238), of ISjeg (nucleotides 2812 to 3618) and of the intergenic region (nucleotides 1604 to 284). The initiation and stop codons of translation are underlined. The potential transcription terminator of the jeg80 gene is indicated by arrows. The inverted repeat sequences defining the ISjeg are boxed in.

FIG. 7 Comparison of the Jeg80 and CryIVD sequences (SEQ ID NO:6,7). The corresponding identical amino acids are boxed in. Functionally equivalent residues are indicated by dots (the conservative replacements are I, L, V and M; D and E; Q and N; K and R; T and S; G and A; and F and Y). The regions similar to the blocks 1 and 4 present in all of the proteins CryI, CryIII and some CryIV are indicated. The vertical arrows represent the cleavage sites for the proteases in the solubilized toxin CryIVD (ref. 11). The numbers indicate the last residue of each line for each protein.

MATERIALS AND METHODS

Bacterial Strains and Plasmids

*E. coli* TG1 {K12, Δ (lac-proAB) supE thi hdsD F' (traD36 proA$^{\pm}$ proB$^{\pm}$ lacZΔ lacI$^{g}$ lacZ ΔM15)} and pHT315 (Arantes, O. et al. (1991) Gene 108:115–119) were used as cloning hosts and vectors, respectively. *B. thuringiensis* ser. *jegathesan* 367 was used to purify the wildtype crystals and the DNA for the cloning experiments. *B. thuringiensis* ser. *thuringiensis* SPL407 (Lereclus, D. et al. (1989) FEMS Microbiol. Lett. 60:211–218) was used as receptor strain for the transformation experiments. The strain *B. thuringiensis* ser. *israelensis* 4Q2-81 (pHT640) was used as source of CryIVD inclusions (Poncet, S. et al. (1993) Appl. Environ. Microbiol. 59:3928–3930).

*B. thuringiensis* SPL407 was transformed by electroporation according to the procedure described in the previously mentioned publication (Lereclus, D. et al.) and *E. coli* was transformed according to the description previously given in the publication by Lederberg, E. M. et al. (1974) J. Bacteriol. 119:1072–1074. The antibiotic concentrations for the bacterial selection were 25 μg/ml of erythromycin and 100 μg/ml of ampicillin.

Handling of the DNA

The restriction enzymes, the DNA T4 ligase and the calf intestine alkaline phosphatase were used as described by Sambrook et al. (Sambrook, J. et al. (1989) a Laboratory Manual, 2nd ed. Cold Spring Harbor Laboratory, Cold Spring Harbor, N.Y.) and according to the instructions of the manufacturers.

The total DNA was isolated from *B. thuringiensis* ser. *jegathesan* according to the description of Delécluse, A. et al. (1991) J. Bacteriol. 173:3374–3381. The DNA of the plasmid was extracted from *E. coli* by a standard alkaline lysis procedure such as that described by Birnboim H. C. et al. (1979) Nucleic Acids Res. 7:1513–1523 and purified further using the Qiagen kit (Qiagen GmbH, Germany). DNA fragments were purified on agarose gel with the DNA purification kit Prep A Gene (BioRad, Hercules, Calif.).

The hybridization experiments were performed on Hybond N$^{+}$ filters (Amersham, Buckinghamshire, United Kingdom). The oligonucleotides were labelled with fluorescein by using the oligonucleotide labelling system ECL 3' Oligolabelling (Amersham).

Starting from plasmids denatured in alkaline medium, the DNA sequences were determined by using the dideoxy chain termination method (Sanger, F. et al. (1977) Proc. Nati. Acad. Sci. USA 74:5463–5467) with the Sequenase kit version 2.0 (U.S. Biochemical Corp., Cleveland, Ohio) and α-$^{35}$S-dATP (>37 TBq/mmol; Amersham). A set of synthetic oligonucleotides (Eurogentec, Belgium) was used to determine the sequence of the two strands.

The software programs of the Genetics Computer Group were used for the sequence analysis (University of Wisconsin, Madison).

SCIENTIFIC RESULTS

1—Polypeptide composition and activity of the Btjeg crystals.

The strain Btjeg 367 was grown in the usual glucose-containing medium at 30° C. with shaking for about 72 hours until the sporulating bacteria lysed. The crystal-spore mixtures were harvested by centrifugation and the crystals were purified on a sucrose gradient according to the procedure described by THOMAS and ELLAR (THOMAS and ELLAR, 1983, J. Cell. Sci. , 60, 181–197). The analysis of the polypeptide composition of these crystals was performed by electrophoresis on SDS-polyacrylamide gel followed by staining with Coomassie blue. The results obtained and presented in FIG. 1 show that the crystals of the Btjeg strain are constituted of several polypeptides of 80, 72, 70, 66, 50, 37 and 28 kDa (some of which might be degradation products).

Immunodetection experiments performed with the aid of a serum directed against the Bti proteins made it possible to demonstrate that the 37 kDa protein is immunologically related to the Bti toxins; a protein of about 100 kDa, undetected on gel after staining with Coomassie blue, also reacts with this serum.

On larvae of *Aedes aegyti, Anopheles stephensi* and *Culex pipiens*, the crystals of this strain exhibit a lower toxicity than that obtained with the Bti crystals but one which is nonetheless considerable, as shown in the following table.

| | LC50 in ng/ml at 24h (confidence interval) on: | | |
|---|---|---|---|
| Crystals | *Aedes aegypti* | *Anopheles stephensi* | *Culex pipiens* |
| Bti 1884 | 20 (16–24) | 39 (29–49) | 20 (14–26) |
| Btjeg 367 | 240 (174–306) | 165 (119–211) | 77 (65–89) |

2—Presence in Btjeg of the Genes Coding for Toxins Having Properties Similar to Those of Bti The total DNA of the strain Btjeg 367 was isolated according to the procedure previously described (DELECLUSE et al., 1991, J. Bacteriol., 173, 3374–3381), then hydrolyzed by the enzyme EcoRI. The fragments obtained were separated by electrophoresis on a 0.6% agarose gel, then transferred to a nylon membrane (Hybond $N^+$, Amersham).

Moreover, the cryIVA, cryIVD and cytA genes of Bti were obtained after hydrolysis of the recombinant plasmids pHT606, pHT611 and pCB4 as indicated in FIG. 2. The DNA fragments containing the Bti genes were purified after separation on an agarose gel then labelled with peroxidase using the "ELC direct nucleic acid" labelling kit (Amersham), and used in hybridization experiments with the hydrolyzed total DNA of the Btjeg strain.

No hybridization was obtained between the DNA of the Btjeg strain and the Bti genes, at least under the hybridization conditions used (80% homology).

3—Cloning of the Genes Coding for the Toxins of the Btjeg Strain a) Determination of the amino acid sequences of the Btjeg proteins.

The amino-terminal sequences of the proteins of 80, 66 and 37 kDa were determined in the microsequencing laboratory of the Pasteur Institute using an automatic sequencer (Applied Biosystems) after transfer of the protein to the Problot membranes (Applied Biosystems); the sequence thus obtained is given in the table below.

Oligonucleotides corresponding to the proteins JEG80, JEG66 and JEG37 (sequences underlined) were synthesized by using the genetic code defined for several genes of *B. thuringiensis* and by incorporating inosine at each ambiguity. The sequence of these oligonucleotides is represented in the table.

| Amino-terminal sequences | Oligonucleotide sequences |
|---|---|
| JEG80:MQNNNFNTTEINNMINFPMY | j80:AATAATATGATIAATTTT CCIATGTA (26-mer) |
| JEG:70:M/XFASYG/XR/DNEY/L | |
| JEG:66:MHYYGNRNEYDILNA | |
| | j66:ATGCATTATTATGGIAATI GIAATGA (26-mer) |
| JEG37:TITNIEIATRDYTNXDXTGE | |
| | j37:AATATIGAAATIGCIACII GIGATTA (26-mer) |

JEG80, SEQ ID NO:11; JEG70, SEQ ID NO:12; JEG66, SEQ ID NO:13; JEG37, SEQ ID NO:14; j80, SEQ ID NO:8; j66, SEQ ID NO:9; j37, SEQ ID NO:10.

In these sequences, "I" represents deoxyinosine, used as neutral base for all positions capable of corresponding to three or four nucleotides.

b) Hybridization of the oligonucleotides to the total DNA of the Btjeg strain.

Hybridization experiments were performed between the oligonucleotides labelled with fluorescein and the total DNA of the Btjeg strain, hydrolyzed by EcoRI, HindIII, XbaI or PstI. The cold probes procedure (3' oligonucleotide labelling system, Amersham) was used. The results obtained are indicated in the table below.

| Oligo-nucleo-tides | Hybridization tempera-ture | Size of the fragments | | | |
|---|---|---|---|---|---|
| | | EcoRI | HindIII | XbaI | PstI |
| j80 | 42° C. | 2 kb | 4 kb | 12 kb | 12 kb |
| j66 | 47° C. | 7 kb | 14 kb | 10 kb | 14 kb |

The probe hybridized specifically at 42° C. to a unique HindIII restriction fragment of about 4 kb and to a unique EcoRI restriction fragment of about 2 kb.

c) Cloning of the gene coding for the protein JEG80.

A DNA library of the Btjeg strain was constructed in *E. coli* TGI by using the bifunctional plasmid pHT315 (ARANTES and LERECLUS, 1991, Gene, 108, 115–119) as cloning vector. The total DNA of the Btjeg strain was hydrolyzed by HindIII, then subjected to electrophoresis on agarose gel. Fragments of about 2 to 6 kb were purified and cloned in this vector. The HindIII fragments of 3 to 5 kb were inserted in the HindIII site of the shuttle vector pHT315 treated with alkaline phosphatase. The recombinant clones produced after transformation of the strain of *E. coli* TGI with the ligation mixtures obtained were tested for their capacity to hybridize with the labelled oligonucleotide j80. Out of the 1,000 recombinant clones obtained, 5 exhibited a positive reaction. A recombinant clone, JEG80.1 was selected and analyzed. This clone contains a 10.9 kb recombinant plasmid (pJEG80.1); the size of the inserted HindIII DNA fragment is 4.3 kb.

4—Analysis of the Recombinant Clone JEG80.1 a) Determination of the restriction map of the plasmid pJEG80.1.

The restriction map of the plasmid pJEG80.1 was determined and is shown in FIG. 3. Hybridization experiments performed with the oligonucleotide j80 made it possible to localize the position of this oligonucleotide on the 4.3 kb HindIII fragment. Moreover, PCR experiments performed with the combinations of oligo-nucleotides j80+universal and j80+reverse made it possible to localize more precisely the start of the gene coding for the protein JEG80 (jeg80) as well as the sense in which it is transcribed (FIG. 3).

b) Determination of the sequence of the jeg80 gene

The nucleotide sequence of the jeg80 gene is determined by the SANGER technique on the plasmid pJEG80.1 previously denatured with sodium hydroxide. The primers used are the oligonucleotide j80, the reverse oligonucleotide or oligonucleotides deduced from the sequences read. A partial sequence (938 bp starting from the 5' end of the gene), is shown in FIG. 4 with the corresponding amino acid sequence.

The pJEG80.1 sequence in the region containing the gene for the 80 kDa protein (designated jeg80) was determined on the two strands (FIG. 5). An open reading frame coding for a polypeptide of 724 residues with a calculated molecular mass of 81, 293 Da has been found. The sequence was examined to determine any region which might be similar to promoter structures of *B. thuringiensis*. No promoter sequence was found in the sequence of about 50 nucleotides upstream from the start codon. Downstream from the stop codon (position 2249 to 2282, FIG. 5) inverted repeat sequences were identified, sequences capable of forming a loop structure with a $\Delta G=-76.9$ kJ/mol calculated according to rules defined by Tinoco et al. (Tinoco, I. J. et al. (1973) Nature (London) New Biol. 246:40–41.

This structure may act as transcription terminator. Twelve nucleotides upstream from the initiation codon a sequence AAAGAAGAGGG (SEQ ID NO:15) was identified as constituting a ribosome binding site (FIG. 5).

An amino acid sequence deduced from the nucleotide sequence obtained was compared with other protein sequences present in the data bank Swiss Prot. This analysis made it possible to demonstrate that the Jeg80 protein exhibits a similarity of the order of 67% with the N-terminal part of the CryIVD protein of Bti; the similarity is about 58% (FIG. 6) with respect to the entire amino acid sequence and somewhat less (36%) with the CryII proteins of Bt kurstaki.

Five blocks are conserved among the toxins CryI, CryIII and most of the CryIV toxins (Höfte, H. et al. (1989) Microbiol. Rev. 53:242–255. However, only block 1 was found in Jeg80 (FIG. 6) with arginine substitutions present in block 4 which was otherwise similar (FIG. 6). Jeg80 possesses a chain of 82 amino acids comprising five cysteine residues at its COOH-terminus, which is absent from CryIVD. The region sensitive to the activity of the CryIVD protease (Dai, S-M et al. (1993) Insect. Biochem. Molec. Biol. 23:273–283) localized in the middle of the protein (amino acids 348–357, FIG. 6) is not conserved in Jeg80.

c) Expression of the jeg80 gene in the strain Bt 407 cry—(also designated as SPL 407).

The plasmid pJEG80.1 was introduced into the strain Bt 407 cry—by electroporation according to the procedure described by LERECLUS et al.(LERECLUS et al. 1989, FEMS Microbiol. Lett. 60, 211–218). A transformant, 407 (pJEG80.1), was selected for additional analysis. During sporulation this clone produces inclusions visible in the optical microscope. No inclusion of this type was present in cells containing the vector pHT315 alone. The expression of jeg80 was analyzed by SDS-PAGE, followed by staining with brilliant Coomassie blue (FIG. 1). The principal polypeptide of the inclusions, purified from the recombinant strain 407 (pJEG80.1), had a molecular weight of about 80 kDa (FIG. 1, line 3), the same as that of the largest polypeptide of the crystals of the wildtype strain 367 (FIG. 1, line 2). These inclusions were purified on a sucrose gradient: they are constituted uniquely of the protein Jeg80 (FIG. 1). Tests were made of immunological reactions between the polypeptide Jeg80 and the proteins of the crystal of *B. thuringiensis* ser *jegathesan, B. thuringiensis* ser *israelensis, B. thuringiensis* ser *medellin* and *darmstadiensis*. The results of the immunological reaction are reported in FIG. 1B. This protein reacts with antibodies directed against the whole crystals of Btjeg as well as with the anti-crystal serum of Bti, and with the anti-total crystal serum of the strain *Bt medellin* (another strain active against mosquitoes, of a new serotype, H30, recently identified).

d) Larvicidal activity of the protein JEG80.

The purified crystals of the strain 407 (pJEG80.1) were tested for their activity against mosquito larvae, in comparison with the crystals derived from the strain Btjeg containing all of the proteins. Assays were also done with the strain 4Q2-81 (pHT 640) which only produces the protein CryIVD. Preliminary results indicate that the protein Jeg80 is active against the three species of mosquitoes tested: *A. aegypti, A. stephensi* and *C. pipiens*. The toxicity of the protein Jeg80 is higher with *C. pipiens* (Table 1). Moreover, the level of toxicity obtained for the protein Jeg80 alone is comparable against *A. stephensi* to that observed with the crystals of Btjeg.

The protein Jeg80 is more toxic than the wildtype strain against *A. aegypti* and equally toxic against *C. pipiens* and *A. stephensi*. In addition and inspite of the similarities to CryIVD, the protein Jeg80 is more toxic than CryIVD: about 10 times more against *A. aegypti* and *A. stephensi* and 40 times more against *C. pipiens.*

The toxic activity was tested under the following conditions: the mosquitoes used were maintained under laboratory conditions at 26° C. in an atmosphere of 80% humidity and with a day-night cycle of 14-10 h. The larvae were subjected to a teatment with dechlorinated water and fed with commercial cat biscuits. The purified inclusions were diluted in plastic cups containing 150 ml of deionized water and assayed in duplicate against 25 stage four *A. aegypti* and *C. pipiens* larvae and 25 stage three *A. stephensi* larvae. Each assay was repeated at least five times. The mortality of the larvae was recorded after 48 hours and the lethal doses ($LC_{50}$) were determined by Probit analysis.

TABLE 1

Toxic activity against mosquitoes of the purified inclusions of different strains of B. thuringiensis

| Strain | Inclusion composition | Toxic activity against the species of mosquitoes ($LC_{50}$ in mg/ml after 48 hours) | | |
|---|---|---|---|---|
| | | A. aegypti | A. stephensi | C. pipiens |
| jegathesan 367 | Wild-type | 47.4 (41.5–54.2) | 54.5 (45.1–99.9) | 9.6 (8.6–10.7) |
| 407(pJEG80.1) | Jeg80 | 18.8 (15.0–23.2) | 42.7 (36.0–50.6) | 10.1 (7.7–13.1) |
| 4Q2-81(pHT640) | CryIVD | 121.5 (96.0–154.0) | 326.0 (265.7–393.3) | 372.4 (301.5–464.1) |

*The values correspond to an average of 5 experiments (see, Materials and Methods). The numbers in parenthesis are the confidence intervals, according to the Probit analysys The cloning and characterization of a new gene from B. thuringiensis, the jeg80 gene of the strain jegathesan 367 has previously been described. The jeg80 gene codes for a protein of 81, 293 Da molecular weight.

The Jeg80 protein is similar to the larvicidal toxin CryIVD of B. thuringiensis ser. israelensis against mosquitoes. It is even the only protein known exhibiting similarities to CryIVD, suggesting that these two proteins have evolved from a common ancestor. The Jeg80 protein also shares a slight similarity to the CryII proteins, comparable to the resemblance existing between CryIV and CryII. However, essential differences exist between Jeg80 and CryIVD, in particular at the carboxy-terminus of the protein. Jeg80 contains a sequence of 82 amino acids including 5 cysteine residues, a sequence which is absent from CryIVD. Bietlot et al. (Bietlot, H. P. et al. (1990) Biochem. J. 267:309–315) have described the importance of such residues for the stability of several δ-endotoxins produced by different strains of B. thuringiensis. This structure might be essential for the formation of the crystal and the insecticidal activity. Mutagenesis might be used to identify the role of this novel carboxy-terminus of Jeg80. There also exist important differences between the flanking regions of the cryIVD and jeg80 genes. The cryIVD gene is the second gene of an operon containing two other genes, p19 and p20 (Adams, L. F. et al. (1989) J. Bacteriol. 171:521–530 and Dervyn, E et al. (1995) J. Bacteriol. 177:2283–2291). Although the corresponding peptides, P19 and P20, are not essential for the expression of CryIVD, they might act as chaperone proteins to stabilize certain constituents of the crystal of B. thuringiensis ser. israelensis (Chang, C. et al. (1993) Appl. Environ. Microbiol. 59:815–821; Dervyn, E. et al. (1995) J. Bacteriol. 177:2283–2291 and Wu, D. et al. (1 994) Mol. Microbiol. 13:965–972). No environment of this type has been recognized for the jeg80 gene: no homology with p20 has been found downstream from jeg80. However, the DNA fragment cloned in the plasmid Jeg80.1 might be too small to contain the initiation site of another gene. Similarly, no gene related to p19 has been found in the 1 kb fragment upstream from Jeg80. On the other hand, at a distance of 550 bp upstream from the jeg80 gene an open reading frame oriented in the opposite direction has been identified. Comparisons of the amino acid sequence deduced with others with the aid of the data bank Swiss Prot has revealed similarities with the transposase of the insertion sequence IS240 of B. thuringiensis ser. israelensis (Delecluse, A. (1989) Plasmid 21:71–78). Two copies of IS240 flank the cryIVA gene in the variety israelensis (Bourgouin, C. et al. (1988) J. Bacteriol. 170:3575–3583) but none was found in the neighbourhood of the cryIVD gene although a variant IS231 was found downstream from the p20 gene (Adams, L. F. et al. (1989) J. Bacteriol. 171:521–530). Insertion elements may be accountable for the dispersal of the toxin genes between the different strains of B. thuringiensis. The cryIVD gene is transcribed starting from two promoters, recognized by the RNA polymerase combined with factor σ35 or σ28 of B. thuringiensis (Dervyn, E. et al. (1995) J. Bacteriol. 177:2283–2291). The sequence analysis of the region upstream from the jeg80 gene has not revealed a consensus promoter for B. thuringiensis. It is possible that jeg80 is transcribed from a promoter recognized by σ factors different from σ35 and σ28 or that the promoter is localized very far upstream from the jeg80 gene, i.e. upstream from the sequence related to the sequence IS240. The protein Jeg80 cross-reacts with antibodies directed against CryIVD and CryIVA. Although the genes jeg80 and cryIVA do not exhibit great similarities, the proteins may nonetheless share similar domains. The Jeg80 protein also reacted with a serum against the total proteins of B. thuringiensis ser. medellin. Preliminary experiments had not revealed polypeptides analogous to the polypeptide CryIVD in this strain (Orduz, D. et al. (1994) Microbiol. Biotechnol. 40:794–799 and Ragni, A. et al. (submitted for publication).

The inclusions composed only of the Jeg80 protein were as toxic as the inclusions of the B. thuringiensis ser. jegathesan wildtype strain against the larvae of the strains C. pipiens and A. stephensis and more toxic than the wildtype strain against the larvae of A. aegypti. This constitutes the first indication of the existence of a protein having a toxic activity against mosquito larvae capable in an isolated form of exhibiting an activity similar to that of a mixture of different polypeptides. In the case of B. thuringiensis ser. israelensis, isolated polypeptides and even combinations of two or three constituents of the crystal are less toxic than the crystals of the wildtype (Angsuthanasombat, C. et al. (1987) Mol. Gen.Genet. 208:384–389; Delecluse, A. et al. (1993) Appl. Environ. Microbiol. 177:2283–2291; Poncet, S. et al. (J. Invertebr. Pathol.: in press) and Wu, D. et al; (1994) Mol. Microbiol. 13:965–972). The high activity of the israelensis strain is due to synergistic interactions between different polypeptides of the crystal. In the case of the strain jegathesan such interactions are not excluded although the Jeg80 protein appears to be a predominant contributor to the toxicity. However, Jeg80 is not the principal constituent of the crystals of jegathesan. Other polypeptides in the crystals, probably the 65 kDa or 37 kDa proteins or both are responsible for the additional activity.

Jeg80 is much more toxic (6 to 40 times more toxic depending on the species of mosquito tested) than CryIVD, inspite of their great similarity. This difference of activity might reflect different modes of action of the two toxins. This difference might be exploited inthe development of insecticides.

We claim:

1. A purified polynucleotide comprising SEQ ID NO:5.

2. A cloning or expression vector, comprising the nucleotide sequence of claim 1.

3. The vector of claim 2, which is the plasmid pJEG 80.1.

4. A prokaryotic or eukaryotic recombinant cell, comprising the cloning or expression vector of claim 2.

5. The polynucleotide of claim 1 comprising nucleotides 325–1260.

6. The polynucleotide of claim 1 comprising nucleotides 1–124.

7. The polynucleotide of claim 1 comprising nucleotides 64–2238.

8. The polynucleotide of claim 1 which encodes a polypeptide having a toxic activity against insects of the Diptera family.

9. The polynucleotide of claim 1 which encodes a polypeptide having a molecular weight of 80 kDa as determined by SDS polyacrlymide gel electrophoresis.

10. A polypeptide encoded by the nucleotide sequence of claim 1.

11. A polypeptide of claim 10, which is encoded by SEQ ID NO:3.

12. (Amended) The polypeptide of claim 11, comprising SEQ ID NO:4 which has a molecular weight of approximately 80 KDa as determined by SDS polyacrlymide gel electrophoresis and has a toxic activity against insects of the Diptera family.

13. A polypeptide having a toxic activity against insects of the Diptera family which reacts with antibodies against the polypeptide of claim 10.

14. A composition having toxic activity against insects of the Diptera family comprising: an effective amount of at least one polypeptide of claim 10.

15. A purified polnucleotide which encodes a first polypeptide which when combined with a second polypeptide encoded by the nucleotide sequence of claim 1 enhances the toxic activity of the second polypeptide against insects of the Diptera family.

16. The polynucleotide of claim 7, which encodes for a polypeptide having a molecular weight of approximately 70 kDa as determined by SDS polyacrlymide gel electrophoresis.

17. A purified polynucleotide which comprises to SEQ ID NO:9 and encodes a first polypeptide, which when combined with a second polypeptide encoded by a nucleotide sequence of claim 1, enhances the toxic activity of the second polypeptide against insects of the Diptera family.

18. The polnucleotide of claim 17, which encodes a polypeptide of about 66 kDa as determined by SDS polyacrlymide gel electrophoresis.

19. A purified polynucleotide which comprises to SEQ ID NO:10 and encodes a first polypeptide, which when, combined with a second polypeptide encoded by a nucleotide sequence of claim 1, enhances the toxic activity of the second polypeptide against insects of the Diptera family.

20. The polynucleotide of claim 19, which encodes for a polypeptide of about 37 kDa as determined by SDS polyacrlymide gel electrophoresis.

21. A purified 4.3 kb Hind III DNA fragment obtained from the plasmid pJEG 80.1.

* * * * *

SEQUENCE LISTING

```
<160> NUMBER OF SEQ ID NOS: 15

<210> SEQ ID NO 1
<211> LENGTH: 1260
<212> TYPE: DNA
<213> ORGANISM: B. thuringiensis ser. jegathesan
<220> FEATURE:
<221> NAME/KEY: CDS
<222> LOCATION: (325)..(1260)

<400> SEQUENCE: 1

gatgtgagga ttattacgtg aatactgatt atgataattt tgaaaagaaa tcatatttgc      60

aaccagaatc atcatatgat tacatgtcag aagaaaatca caaagttcca ttaattagat     120

gtgaattcct atttttattt cagtccagaa tcctgaataa tggaaattaa atgcacccta     180

tgatttataa atatatgtac ctttaaaaca agaataatta taactgtata aaaataggta     240

tactattgga aaacaaaaaa gttaattatg aaaagatttc gtttatatta gtaaattgtt     300

taaagaagag ggggcatgtt ttaa atg caa aat aac aac ttt aat acc aca       351
                           Met Gln Asn Asn Asn Phe Asn Thr Thr
                             1               5

gaa att aat aat atg att aat ttc cct atg tat aat ggt aga tta gaa      399
Glu Ile Asn Asn Met Ile Asn Phe Pro Met Tyr Asn Gly Arg Leu Glu
 10                  15                  20                  25

cct tct cta gct cca gca tta ata gca gta gct cca att gct aaa tat      447
Pro Ser Leu Ala Pro Ala Leu Ile Ala Val Ala Pro Ile Ala Lys Tyr
                 30                  35                  40

tta gca aca gct ctt gct aaa tgg gct gta aaa caa ggg ttt gca aaa      495
Leu Ala Thr Ala Leu Ala Lys Trp Ala Val Lys Gln Gly Phe Ala Lys
             45                  50                  55

tta aaa tcc gag ata ttc ccc ggt aat acg cct gct act atg gat aag      543
Leu Lys Ser Glu Ile Phe Pro Gly Asn Thr Pro Ala Thr Met Asp Lys
         60                  65                  70

gtt cgt att gag gta caa aca ctt tta gac caa aga tta caa gat gac      591
Val Arg Ile Glu Val Gln Thr Leu Leu Asp Gln Arg Leu Gln Asp Asp
     75                  80                  85

aga gtt aag att tta gaa ggt gaa tac aaa gga att att gac gtg agt      639
Arg Val Lys Ile Leu Glu Gly Glu Tyr Lys Gly Ile Ile Asp Val Ser
 90                  95                 100                 105

aaa gtt ttt act gat tat gtt aat caa tct aaa ttt gag act gga aca      687
Lys Val Phe Thr Asp Tyr Val Asn Gln Ser Lys Phe Glu Thr Gly Thr
                110                 115                 120

gct aat agg ctt ttt ttt gat aca agt aac caa tta ata agc aga ttg      735
Ala Asn Arg Leu Phe Phe Asp Thr Ser Asn Gln Leu Ile Ser Arg Leu
            125                 130                 135

cct caa ttt gag att gca gga tat gaa gga gta tcc att tca ctt ttt      783
Pro Gln Phe Glu Ile Ala Gly Tyr Glu Gly Val Ser Ile Ser Leu Phe
        140                 145                 150

act cag atg tgt aca ttt cat ttg ggt tta tta aaa gat gga att tta      831
Thr Gln Met Cys Thr Phe His Leu Gly Leu Leu Lys Asp Gly Ile Leu
    155                 160                 165

gca gga agc gat tgg gga ttt gct cct gca gat aaa gac gct ctt att      879
Ala Gly Ser Asp Trp Gly Phe Ala Pro Ala Asp Lys Asp Ala Leu Ile
170                 175                 180                 185

tgc caa ttc aat aga ttt gtc aat gaa tat aat act cga ctg atg gta      927
Cys Gln Phe Asn Arg Phe Val Asn Glu Tyr Asn Thr Arg Leu Met Val
                190                 195                 200
```

-continued

```
ttg tac tca aaa gaa ttt gga cgg tta tta gca aaa aat ctt aat gaa      975
Leu Tyr Ser Lys Glu Phe Gly Arg Leu Leu Ala Lys Asn Leu Asn Glu
            205                 210                 215

gcc ttg aac ttt aga aat atg tgt agt tta tat gtc ttt cct ttt tct     1023
Ala Leu Asn Phe Arg Asn Met Cys Ser Leu Tyr Val Phe Pro Phe Ser
        220                 225                 230

gaa gca tgg tct tta tta agg tat gaa gga aca aaa tta gaa aac acg     1071
Glu Ala Trp Ser Leu Leu Arg Tyr Glu Gly Thr Lys Leu Glu Asn Thr
    235                 240                 245

ctt tca tta tgg aat ttt gtg ggt gaa agt atc aat aat ata tct cct     1119
Leu Ser Leu Trp Asn Phe Val Gly Glu Ser Ile Asn Asn Ile Ser Pro
250                 255                 260                 265

aat gat tgg aaa ggt gcg ctt tat aaa ttg tta atg gga gca cct aat     1167
Asn Asp Trp Lys Gly Ala Leu Tyr Lys Leu Leu Met Gly Ala Pro Asn
            270                 275                 280

caa aga tta aac aat gtt aag ttt aat tat agt tat ttt tct gat act     1215
Gln Arg Leu Asn Asn Val Lys Phe Asn Tyr Ser Tyr Phe Ser Asp Thr
            285                 290                 295

caa gcg aca ata cat cgt gaa aac att cat ggt gtc ctg cca aca         1260
Gln Ala Thr Ile His Arg Glu Asn Ile His Gly Val Leu Pro Thr
        300                 305                 310


<210> SEQ ID NO 2
<211> LENGTH: 312
<212> TYPE: PRT
<213> ORGANISM: B. thuringiensis ser. jegathesan

<400> SEQUENCE: 2

Met Gln Asn Asn Asn Phe Asn Thr Thr Glu Ile Asn Asn Met Ile Asn
  1               5                  10                  15

Phe Pro Met Tyr Asn Gly Arg Leu Glu Pro Ser Leu Ala Pro Ala Leu
            20                  25                  30

Ile Ala Val Ala Pro Ile Ala Lys Tyr Leu Ala Thr Ala Leu Ala Lys
        35                  40                  45

Trp Ala Val Lys Gln Gly Phe Ala Lys Leu Lys Ser Glu Ile Phe Pro
    50                  55                  60

Gly Asn Thr Pro Ala Thr Met Asp Lys Val Arg Ile Glu Val Gln Thr
 65                  70                  75                  80

Leu Leu Asp Gln Arg Leu Gln Asp Asp Arg Val Lys Ile Leu Glu Gly
                85                  90                  95

Glu Tyr Lys Gly Ile Ile Asp Val Ser Lys Val Phe Thr Asp Tyr Val
            100                 105                 110

Asn Gln Ser Lys Phe Glu Thr Gly Thr Ala Asn Arg Leu Phe Phe Asp
        115                 120                 125

Thr Ser Asn Gln Leu Ile Ser Arg Leu Pro Gln Phe Glu Ile Ala Gly
    130                 135                 140

Tyr Glu Gly Val Ser Ile Ser Leu Phe Thr Gln Met Cys Thr Phe His
145                 150                 155                 160

Leu Gly Leu Leu Lys Asp Gly Ile Leu Ala Gly Ser Asp Trp Gly Phe
                165                 170                 175

Ala Pro Ala Asp Lys Asp Ala Leu Ile Cys Gln Phe Asn Arg Phe Val
            180                 185                 190

Asn Glu Tyr Asn Thr Arg Leu Met Val Leu Tyr Ser Lys Glu Phe Gly
        195                 200                 205

Arg Leu Leu Ala Lys Asn Leu Asn Glu Ala Leu Asn Phe Arg Asn Met
    210                 215                 220
```

-continued

```
Cys Ser Leu Tyr Val Phe Pro Phe Ser Glu Ala Trp Ser Leu Leu Arg
225                 230                 235                 240

Tyr Glu Gly Thr Lys Leu Glu Asn Thr Leu Ser Leu Trp Asn Phe Val
                245                 250                 255

Gly Glu Ser Ile Asn Asn Ile Ser Pro Asn Asp Trp Lys Gly Ala Leu
            260                 265                 270

Tyr Lys Leu Leu Met Gly Ala Pro Asn Gln Arg Leu Asn Asn Val Lys
        275                 280                 285

Phe Asn Tyr Ser Tyr Phe Ser Asp Thr Gln Ala Thr Ile His Arg Glu
    290                 295                 300

Asn Ile His Gly Val Leu Pro Thr
305                 310


<210> SEQ ID NO 3
<211> LENGTH: 2434
<212> TYPE: DNA
<213> ORGANISM: B. thuringiensis ser. jegathesan

<400> SEQUENCE: 3

ttaattatga aaagatttcg tttatattag taaattgttt aaagaagagg gggcatgttt     60

taaatgcaaa ataacaactt taataccaca gaaattaata atatgattaa tttccctatg    120

tataatggta gattagaacc ttctctagct ccagcattaa tagcagtagc tccaattgct    180

aaatatttag caacagctct tgctaaatgg gctgtaaaac aagggtttgc aaaattaaaa    240

tccgagatat tccccggtaa tacgcctgct actatggata aggttcgtat tgaggtacaa    300

acacttttag accaaagatt acaagatgac agagttaaga ttttagaagg tgaatacaaa    360

ggaattattg acgtgagtaa agtttttact gattatgtta atcaatctaa atttgagact    420

ggaacagcta ataggctttt ttttgataca agtaaccaat taataagcag attgcctcaa    480

tttgagattg caggatatga aggagtatcc atttcacttt ttactcagat gtgtacattt    540

catttgggtt tattaaaaga tggaatttta gcaggaagcg attggggatt tgctcctgca    600

gataaagacg ctcttatttg ccaattcaat agatttgtca atgaatataa tactcgactg    660

atggtattgt actcaaaaga atttggacgg ttattagcaa aaaatcttaa tgaagccttg    720

aactttagaa atatgtgtag tttatatgtc tttccttttt ctgaagcatg gtctttatta    780

aggtatgaag gaacaaaatt agaaaacacg ctttcattat ggaattttgt gggtgaaagt    840

atcaataata tatctcctaa tgattggaaa ggtgcgcttt ataaattgtt aatgggagca    900

cctaatcaaa gattaaacaa tgttaagttt aattatagtt atttttctga tactcaagcg    960

acaatacatc gtgaaaacat tcatggtgtc ctgccaacat ataatggagg accaacaatt   1020

acaggatgga tagggaatgg gcgtttcagc ggacttagtt ttccttgtag taatgaatta   1080

gaaattacaa aaataaaaca ggaaataact tacaatgata aagggggaaa tttcaattca   1140

atagttcctg ctgctacgcg caatgaaatt ctaactgcta ccgttccaac atcagctgat   1200

ccattttttta aaaccgctga tattaactgg aaatatttct ctccgggtct ttactctgga   1260

tggaatatta aatttgatga tacagtcact ttaaaaagta gagtaccaag tattatacct   1320

tcaaatatat taaagtatga tgattattat attcgtgccg tttcagcctg tccaaaaggc   1380

gtatcacttg catataacca tgattttta acgttaacat ataataaatt agaatatgat   1440

gcacctacta cacaaaatat cattgtagga ttttcaccag ataatactaa gagtttttat   1500

aggagcaact ctcattatct aagtacaaca gatgatgcct atgtaattcc tgctttacaa   1560

ttttctacag tctcagatag atcattctta gaagatacac cagatcaagc aacagatggc   1620
```

-continued agtattaaat ttacggatac tgttcttggg aatgaggcaa aatattctat tagactaaat 1680
actggattta atacagctac taggtataga ttaattatac gttttaaagc gcctgctcgt 1740
ttggctgctg gtatacgtgt acgttctcaa aattcaggga ataataagtt attaggtggt 1800
attcctgtag agggtaattc tggatggata gattatatta cagattcatt tacttttgat 1860
gaccttggga ttacaacttc aagtacaaat gctttcttta gtattgattc agatggtgta 1920
aatgcttctc aacaatggta tttgtctaaa ttaattttag taaaagaatc cagttttacg 1980
actcagattc cattaaaacc atacgttatt gtacgttgtc cggatacttt ttttgtgagc 2040
aacaattcaa gtagtacgta cgaacaaggc tataacaaca attacaacca gaattctagc 2100
agtatgtacg atcaaggcta taacaatagc tataatccaa actctggttg tacgtgtaat 2160
caagactata acaatagcta taaccaaaac tctggctgta catgtaacca agggtataac 2220
aataactatc ctaaataaga aaacaatgaa aaagcattcc cctctcacaa ggaatgcttt 2280
tttgtctgcc ctattttacg catatataaa acccattggt aattgcatac tatgcatact 2340
ctataaaacc gttccatcct acccctgtta tgaagtgacc tttgtcaata gtttttcaac 2400
cataatattt tttcttgatg gcatacaaaa gctt 2434

<210> SEQ ID NO 4
<211> LENGTH: 724
<212> TYPE: PRT
<213> ORGANISM: B. thuringiensis ser. jegathesan

<400> SEQUENCE: 4

Met Gln Asn Asn Asn Phe Asn Thr Thr Glu Ile Asn Asn Met Ile Asn
1 5 10 15

Phe Pro Met Tyr Asn Gly Arg Leu Glu Pro Ser Leu Ala Pro Ala Leu
20 25 30

Ile Ala Val Ala Pro Ile Ala Lys Tyr Leu Ala Thr Ala Leu Ala Lys
35 40 45

Trp Ala Val Lys Gln Gly Phe Ala Lys Leu Lys Ser Glu Ile Phe Pro
50 55 60

Gly Asn Thr Pro Ala Thr Met Asp Lys Val Arg Ile Glu Val Gln Thr
65 70 75 80

Leu Leu Asp Gln Arg Leu Gln Asp Asp Arg Val Lys Ile Leu Glu Gly
85 90 95

Glu Tyr Lys Gly Ile Ile Asp Val Ser Lys Val Phe Thr Asp Tyr Val
100 105 110

Asn Gln Ser Lys Phe Glu Thr Gly Thr Ala Asn Arg Leu Phe Phe Asp
115 120 125

Thr Ser Asn Gln Leu Ile Ser Arg Leu Pro Gln Phe Glu Ile Ala Gly
130 135 140

Tyr Glu Gly Val Ser Ile Ser Leu Phe Thr Gln Met Cys Thr Phe His
145 150 155 160

Leu Gly Leu Leu Lys Asp Gly Ile Leu Ala Gly Ser Asp Trp Gly Phe
165 170 175

Ala Pro Ala Asp Lys Asp Ala Leu Ile Cys Gln Phe Asn Arg Phe Val
180 185 190

Asn Glu Tyr Asn Thr Arg Leu Met Val Leu Tyr Ser Lys Glu Phe Gly
195 200 205

Arg Leu Leu Ala Lys Asn Leu Asn Glu Ala Leu Asn Phe Arg Asn Met
210 215 220

-continued

```
Cys Ser Leu Tyr Val Phe Pro Phe Ser Glu Ala Trp Ser Leu Leu Arg
225                 230                 235                 240

Tyr Glu Gly Thr Lys Leu Glu Asn Thr Leu Ser Leu Trp Asn Phe Val
                245                 250                 255

Gly Glu Ser Ile Asn Asn Ile Ser Pro Asn Asp Trp Lys Gly Ala Leu
            260                 265                 270

Tyr Lys Leu Leu Met Gly Ala Pro Asn Gln Arg Leu Asn Asn Val Lys
        275                 280                 285

Phe Asn Tyr Ser Tyr Phe Ser Asp Thr Gln Ala Thr Ile His Arg Glu
    290                 295                 300

Asn Ile His Gly Val Leu Pro Thr Tyr Asn Gly Gly Pro Thr Ile Thr
305                 310                 315                 320

Gly Trp Ile Gly Asn Gly Arg Phe Ser Gly Leu Ser Phe Pro Cys Ser
                325                 330                 335

Asn Glu Leu Glu Ile Thr Lys Ile Lys Gln Glu Ile Thr Tyr Asn Asp
            340                 345                 350

Lys Gly Gly Asn Phe Asn Ser Ile Val Pro Ala Ala Thr Arg Asn Glu
        355                 360                 365

Ile Leu Thr Ala Thr Val Pro Thr Ser Ala Asp Pro Phe Phe Lys Thr
    370                 375                 380

Ala Asp Ile Asn Trp Lys Tyr Phe Ser Pro Gly Leu Tyr Ser Gly Trp
385                 390                 395                 400

Asn Ile Lys Phe Asp Asp Thr Val Thr Leu Lys Ser Arg Val Pro Ser
                405                 410                 415

Ile Ile Pro Ser Asn Ile Leu Lys Tyr Asp Asp Tyr Tyr Ile Arg Ala
            420                 425                 430

Val Ser Ala Cys Pro Lys Gly Val Ser Leu Ala Tyr Asn His Asp Phe
        435                 440                 445

Leu Thr Leu Thr Tyr Asn Lys Leu Glu Tyr Asp Ala Pro Thr Thr Gln
    450                 455                 460

Asn Ile Ile Val Gly Phe Ser Pro Asp Asn Thr Lys Ser Phe Tyr Arg
465                 470                 475                 480

Ser Asn Ser His Tyr Leu Ser Thr Thr Asp Asp Ala Tyr Val Ile Pro
                485                 490                 495

Ala Leu Gln Phe Ser Thr Val Ser Asp Arg Ser Phe Leu Glu Asp Thr
            500                 505                 510

Pro Asp Gln Ala Thr Asp Gly Ser Ile Lys Phe Thr Asp Thr Val Leu
        515                 520                 525

Gly Asn Glu Ala Lys Tyr Ser Ile Arg Leu Asn Thr Gly Phe Asn Thr
    530                 535                 540

Ala Thr Arg Tyr Arg Leu Ile Ile Arg Phe Lys Ala Pro Ala Arg Leu
545                 550                 555                 560

Ala Ala Gly Ile Arg Val Arg Ser Gln Asn Ser Gly Asn Asn Lys Leu
                565                 570                 575

Leu Gly Gly Ile Pro Val Glu Gly Asn Ser Gly Trp Ile Asp Tyr Ile
            580                 585                 590

Thr Asp Ser Phe Thr Phe Asp Asp Leu Gly Ile Thr Thr Ser Ser Thr
        595                 600                 605

Asn Ala Phe Phe Ser Ile Asp Ser Asp Gly Val Asn Ala Ser Gln Gln
    610                 615                 620

Trp Tyr Leu Ser Lys Leu Ile Leu Val Lys Glu Ser Ser Phe Thr Thr
625                 630                 635                 640
```

-continued

```
Gln Ile Pro Leu Lys Pro Tyr Val Ile Val Arg Cys Pro Asp Thr Phe
                645                 650                 655

Phe Val Ser Asn Asn Ser Ser Ser Thr Tyr Glu Gln Gly Tyr Asn Asn
            660                 665                 670

Asn Tyr Asn Gln Asn Ser Ser Ser Met Tyr Asp Gln Gly Tyr Asn Asn
        675                 680                 685

Ser Tyr Asn Pro Asn Ser Gly Cys Thr Cys Asn Gln Asp Tyr Asn Asn
    690                 695                 700

Ser Tyr Asn Gln Asn Ser Gly Cys Thr Cys Asn Gln Gly Tyr Asn Asn
705                 710                 715                 720

Asn Tyr Pro Lys


<210> SEQ ID NO 5
<211> LENGTH: 3675
<212> TYPE: DNA
<213> ORGANISM: B. thuringiensis ser. jegathesan

<400> SEQUENCE: 5

actgtttcca gtgaagtatt gtccccatcc taccttgcca aaatatctca tacgtatcat     60

acgttaatgg ttacccaaaa tatatacgca ttttatcccg tctgtttttt cgtaaggaac    120

actctcccct tacgaaaaag taacaaaaga ataaatccta tcaataacaa tatgggaacc    180

aatgtacatg tcggtctcaa aaccaatatc gataacaata tcagaactaa tgtgcatgtt    240

ggtctcaaac ctaatatcga taacaatatc ggaactagca tgtatgacga tcttaagacc    300

aacattaaca acaatatcgg aacaagcatg catgatgaac ttaacaacga gtgttttttt    360

cataggcctg ttgcatgtta ttgcatacca aaattacctt agactcagca ttttgaccta    420

agaaaatgat tttaattaaa tctgtttatg gtaacaactc ttcgtaaatg tggtagactt    480

agttatgatt tctttcgtaa acatgaactt caacattagg gttccagtag ttttcattta    540

cttagacatt atattagata ggtaggtctt aatgggagat gtccttatgg tggattattg    600

aataataagg gacttaaaac tcttgcatgt gcatatggtc gtcggtttgc tcgtccgcga    660

aattttgcat attaattaga tatggatcat cgacataatt taggtcataa atcagattat    720

cttataaaac ggagtaaggg ttcttgtcat aggcatttaa attatgacgg tagacaacga    780

actagaccac atagaagatt cttactagat agactctgac atcttttaac atttcgtcct    840

taatgtatcc gtagtagaca acatgaatct attactctca acgaggatat ttttgagaat    900

cataatagac cacttttagg atgttactat aaaacacatc atccacgtag tataagatta    960

aataatatac aattgcaatt ttttagtacc aatatacgtt cactatgcgg aaaacctgtc   1020

cgactttgcc gtgcttatat tattagtagt atgaaattat ataaacttcc atattatgaa   1080

ccatgagatg aaaaatttca ctgacatagt agtttaaatt ataaggtagg tctcatttct   1140

gggcctctct ttataaaggt caattatagt cgccaaaatt ttttacctag tcgactacaa   1200

ccttgccatc gtcaatctta aagtaacgcg catcgtcgtc cttgataact taactttaaa   1260

gggggaaata gtaacattca ataaaggaca aaataaaaac attaaagatt aagtaatgat   1320

gttccttttg attcaggcga ctttgcgggt aagggatagg taggacatta acaaccagga   1380

ggtaatatac aaccgtcctg tggtacttac aaaagtgcta cataacagcg aactcatagt   1440

ctttttattg atattaattt gaattgtaac aaattagaaa ctaatccacg agggtaattg   1500

ttaaatattt cgcgtggaaa ggttagtaat cctctatata ataactatga aagtgggtgt   1560

tttaaggtat tactttcgca caaaagatta aaacaaggaa gtatggaatt atttctggta   1620
```

-continued

```
cgaagtcttt ttcctttctg tatatttgat gtgtataaag atttcaagtt ccgaagtaat   1680
tctaaaaaac gattattggc aggtttaaga aaactcatgt tatggtagtc agctcataat   1740
ataagtaact gtttagataa cttaaccgtt tattctcgca gaaatagacg tcctcgttta   1800
ggggttagcg aaggacgatt ttaaggtaga aaattatttg ggtttacttt acatgtgtag   1860
actcattttt cactttacct atgaggaagt ataggacgtt agagtttaac tccgttagac   1920
gaataattaa ccaatgaaca tagttttttt tcggataatc gacaaggtca gagtttaaat   1980
ctaactaatt gtattagtca tttttgaaat gagtgcagtt attaaggaaa cataagtgga   2040
agattttaga attgagacag tagaacatta gaaaccagat tttcacaaac atggagttat   2100
gcttggaata ggtatcatcg tccgcataat ggccccttat agagcctaaa attaaaacgt   2160
ttgggaacaa aatgtcgggt aaatcgttct cgacaacgat ttataaatcg ttaacctcga   2220
tgacgataat tacgacctcg atctcttcca agattagatg gtaatatgta tccctttaat   2280
tagtataata attaaagaca ccataatttc aacaataaaa cgtaaatttt gtacggggga   2340
gaagaaattt gttaaatgat tatatttgct ttagaaaagt attaattgaa aaaacaaaag   2400
gttatcatat ggataaaaat atgtcaatat taataagaac aaaatttcca tgtatataaa   2460
tatttagtat cccacgtaaa ttaaaggtaa taagtcctaa gacctgactt tatttttatc   2520
cttaagtgta gattaattac cttgaaacac taaaagaaga ctgtacatta gtatactact   2580
aagaccaacg tttatactaa agaaaagttt taatagtatt agtcataagt gcattattag   2640
gagtgtagga aaagataaaa gtgaagataa agcagttagc aatcaaataa aggacaaaaa   2700
aattaaacaa tagaaaaacg tggtctttgt ttttttggac gtatacgccc taaacatatg   2760
tgaagtttca gtgtggacca gttaggaaaa aatgcgtctc ataatggttt cccaagacaa   2820
cgtttcaaga aaagtcgacc aatgttaaat ctttttcgac actcctctta acgtttaccc   2880
tataaaattt ccttttgtta agttctttct ataataaaaa catcggcaac cgatgataac   2940
agcaaaaaga aattcgatag cactacatag actttaagac tttcttgctc cgcaaaggca   3000
agtgggttgt tgttagtacg ctacccacgt acttataccg ttagactaga tagtttagac   3060
ctttttcttt ttgtgttgta gagttagcag taccgtaaat ctactttgca tatagtttca   3120
gtttccgctt accacgatag atatagcacg ataactatca ctacctgtat gcgaactaaa   3180
agttgaagca gtttgtgcgc tagtagttcg gcgaatatac aaatactttg ctaatcactt   3240
ttgaaaacct cttggtttcc aagaataatg tctattccga ggacgtgacg aaacacgcaa   3300
attttttgat tttttcttgc cacacataca cgtatgtttt gtaacatgcc aatttgtaga   3360
attattggac taacttgttc tggtggctgt acattttgct gcaaaacggt ttagaagacc   3420
taaggtttta taggcggtac gaagtgcatg gtattttccc taactttgct aagtccggaa   3480
tatatttgtc tctgcttcaa acttagtctg aggcagaaaa gacgcatgtt acttgacgtt   3540
gttaatgatc gctgacgaat tgataaagag tagtaaaagg ttccgcaaat atgaaaaaag   3600
tttgaaacgt tgtcttggag tacggaatat ataaaatgaa gtctttctaa ttggcaatga   3660
actcttccta gtgaa                                                    3675
```

<210> SEQ ID NO 6
<211> LENGTH: 725
<212> TYPE: PRT
<213> ORGANISM: B. thuringiensis ser. jegathesan

<400> SEQUENCE: 6

-continued

```
Met Met Gln Asn Asn Asn Phe Asn Thr Thr Glu Ile Asn Asn Met Ile
  1               5                  10                  15

Asn Phe Pro Met Tyr Asn Gly Arg Leu Glu Pro Ser Leu Ala Pro Ala
             20                  25                  30

Leu Ile Ala Val Ala Pro Ile Ala Lys Tyr Leu Ala Thr Ala Leu Ala
         35                  40                  45

Lys Trp Ala Val Lys Gln Gly Phe Ala Lys Leu Lys Ser Glu Ile Phe
     50                  55                  60

Pro Gly Asn Thr Pro Ala Thr Met Asp Lys Val Arg Ile Glu Val Gln
 65                  70                  75                  80

Thr Leu Leu Asp Gln Arg Leu Gln Asp Asp Arg Val Lys Ile Leu Glu
                 85                  90                  95

Gly Glu Tyr Lys Gly Ile Ile Asp Val Ser Lys Val Phe Thr Asp Tyr
            100                 105                 110

Val Asn Gln Ser Lys Phe Glu Thr Gly Thr Ala Asn Arg Leu Phe Phe
        115                 120                 125

Asp Thr Ser Asn Gln Leu Ile Ser Arg Leu Pro Gln Phe Glu Ile Ala
    130                 135                 140

Gly Tyr Glu Gly Val Ser Ile Ser Leu Phe Thr Gln Met Cys Thr Phe
145                 150                 155                 160

His Leu Gly Leu Leu Lys Asp Gly Ile Leu Ala Gly Ser Asp Trp Gly
                165                 170                 175

Phe Ala Pro Ala Asp Lys Asp Ala Leu Ile Cys Gln Phe Asn Arg Phe
            180                 185                 190

Val Asn Glu Tyr Asn Thr Arg Leu Met Val Leu Tyr Ser Lys Glu Phe
        195                 200                 205

Gly Arg Leu Leu Ala Lys Asn Leu Asn Glu Ala Leu Asn Phe Arg Asn
    210                 215                 220

Met Cys Ser Leu Tyr Val Phe Pro Phe Ser Glu Ala Trp Ser Leu Leu
225                 230                 235                 240

Arg Tyr Glu Gly Thr Lys Leu Glu Asn Thr Leu Ser Leu Trp Asn Phe
                245                 250                 255

Val Gly Glu Ser Ile Asn Asn Ile Ser Pro Asn Asp Trp Lys Gly Ala
            260                 265                 270

Leu Tyr Lys Leu Leu Met Gly Ala Pro Asn Gln Arg Leu Asn Asn Val
        275                 280                 285

Lys Phe Asn Tyr Ser Tyr Phe Ser Asp Thr Gln Ala Thr Ile His Arg
    290                 295                 300

Glu Asn Ile His Gly Val Leu Pro Thr Tyr Asn Gly Gly Pro Thr Ile
305                 310                 315                 320

Thr Gly Trp Ile Gly Asn Gly Arg Phe Ser Gly Leu Ser Phe Pro Cys
                325                 330                 335

Ser Asn Glu Leu Glu Ile Thr Lys Ile Lys Gln Glu Ile Thr Tyr Asn
            340                 345                 350

Asp Lys Gly Gly Asn Phe Asn Ser Ile Val Pro Ala Ala Thr Arg Asn
        355                 360                 365

Glu Ile Leu Thr Ala Thr Val Pro Thr Ser Ala Asp Pro Phe Phe Lys
    370                 375                 380

Thr Ala Asp Ile Asn Trp Lys Tyr Phe Ser Pro Gly Leu Tyr Ser Gly
385                 390                 395                 400

Trp Asn Ile Lys Phe Asp Asp Thr Val Thr Leu Lys Ser Arg Val Pro
                405                 410                 415
```

-continued

```
Ser Ile Ile Pro Ser Asn Ile Leu Lys Tyr Asp Asp Tyr Tyr Ile Arg
            420                 425                 430

Ala Val Ser Ala Cys Pro Lys Gly Val Ser Leu Ala Tyr Asn His Asp
        435                 440                 445

Phe Leu Thr Leu Thr Tyr Asn Lys Leu Glu Tyr Asp Ala Pro Thr Thr
    450                 455                 460

Gln Asn Ile Ile Val Gly Phe Ser Pro Asp Asn Thr Lys Ser Phe Tyr
465                 470                 475                 480

Arg Ser Asn Ser His Tyr Leu Ser Thr Thr Asp Asp Ala Tyr Val Ile
                485                 490                 495

Pro Ala Leu Gln Phe Ser Thr Val Ser Asp Arg Ser Phe Leu Glu Asp
            500                 505                 510

Thr Pro Asp Gln Ala Thr Asp Gly Ser Ile Lys Phe Thr Asp Thr Val
        515                 520                 525

Leu Gly Asn Glu Ala Lys Tyr Ser Ile Arg Leu Asn Thr Gly Phe Asn
    530                 535                 540

Thr Ala Thr Arg Tyr Arg Leu Ile Ile Arg Phe Lys Ala Pro Ala Arg
545                 550                 555                 560

Leu Ala Ala Gly Ile Arg Val Arg Ser Gln Asn Ser Gly Asn Asn Lys
                565                 570                 575

Leu Leu Gly Gly Ile Pro Val Glu Gly Asn Ser Gly Trp Ile Asp Tyr
            580                 585                 590

Ile Thr Asp Ser Phe Thr Phe Asp Asp Leu Gly Ile Thr Thr Ser Ser
        595                 600                 605

Thr Asn Ala Phe Phe Ser Ile Asp Ser Asp Gly Val Asn Ala Ser Gln
    610                 615                 620

Gln Trp Tyr Leu Ser Lys Leu Ile Leu Val Lys Glu Ser Ser Phe Thr
625                 630                 635                 640

Thr Gln Ile Pro Leu Lys Pro Tyr Val Ile Val Arg Cys Pro Asp Thr
                645                 650                 655

Phe Phe Val Ser Asn Asn Ser Ser Ser Thr Tyr Glu Gln Gly Tyr Asn
            660                 665                 670

Asn Asn Tyr Asn Gln Asn Ser Ser Ser Met Tyr Asp Gln Gly Tyr Asn
        675                 680                 685

Asn Ser Tyr Asn Pro Asn Ser Gly Cys Thr Cys Asn Gln Asp Tyr Asn
    690                 695                 700

Asn Ser Tyr Asn Gln Asn Ser Gly Cys Thr Cys Asn Gln Gly Tyr Asn
705                 710                 715                 720

Asn Asn Tyr Pro Lys
                725


<210> SEQ ID NO 7
<211> LENGTH: 644
<212> TYPE: PRT
<213> ORGANISM: B. thuringiensis ser. israelensis

<400> SEQUENCE: 7

Met Met Glu Asp Ser Ser Leu Asp Thr Leu Ser Ile Val Asn Glu Thr
  1               5                  10                  15

Asp Phe Pro Leu Tyr Asn Asn Tyr Thr Glu Pro Thr Ile Ala Pro Ala
             20                  25                  30

Leu Ile Ala Val Ala Pro Ile Ala Gln Tyr Leu Ala Thr Ala Ile Gly
         35                  40                  45

Lys Trp Ala Ala Lys Ala Ala Phe Ser Lys Val Leu Ser Leu Ile Phe
     50                  55                  60
```

-continued

```
Pro Gly Ser Gln Pro Ala Thr Met Glu Lys Val Arg Thr Glu Val Glu
 65                 70                  75                  80

Thr Leu Ile Asn Gln Lys Leu Ser Gln Asp Arg Val Asn Ile Leu Asn
                85                  90                  95

Ala Glu Tyr Arg Gly Ile Ile Glu Val Ser Asp Val Phe Asp Ala Tyr
            100                 105                 110

Ile Lys Gln Pro Gly Phe Thr Pro Ala Thr Ala Lys Gly Tyr Phe Leu
        115                 120                 125

Asn Leu Ser Gly Ala Ile Ile Gln Arg Leu Pro Gln Phe Glu Val Gln
    130                 135                 140

Thr Tyr Glu Gly Val Ser Ile Ala Leu Phe Thr Gln Met Cys Thr Leu
145                 150                 155                 160

His Leu Thr Leu Leu Lys Asp Gly Ile Leu Ala Gly Ser Ala Trp Gly
                165                 170                 175

Phe Thr Gln Ala Asp Val Asp Ser Phe Ile Lys Leu Phe Asn Gln Lys
            180                 185                 190

Val Leu Asp Tyr Arg Thr Arg Leu Met Arg Met Tyr Thr Glu Glu Phe
        195                 200                 205

Gly Arg Leu Cys Lys Val Ser Leu Lys Asp Gly Leu Thr Phe Arg Asn
    210                 215                 220

Met Cys Asn Leu Tyr Val Phe Pro Phe Ala Glu Ala Trp Ser Leu Met
225                 230                 235                 240

Arg Tyr Glu Gly Leu Lys Leu Gln Ser Ser Leu Ser Leu Trp Asp Tyr
                245                 250                 255

Val Gly Val Ser Ile Pro Val Asn Tyr Asn Glu Trp Gly Gly Leu Val
            260                 265                 270

Tyr Lys Leu Leu Met Gly Glu Val Asn Gln Arg Leu Thr Thr Val Lys
        275                 280                 285

Phe Asn Tyr Ser Phe Thr Asn Glu Pro Ala Asp Ile Pro Ala Arg Glu
    290                 295                 300

Asn Ile Arg Gly Val His Pro Ile Tyr Asp Pro Ser Ser Gly Leu Thr
305                 310                 315                 320

Gly Trp Ile Gly Asn Gly Arg Thr Asn Asn Phe Asn Phe Ala Asp Asn
                325                 330                 335

Asn Gly Asn Glu Ile Met Glu Val Arg Thr Gln Thr Phe Tyr Gln Asn
            340                 345                 350

Pro Asn Asn Glu Pro Ile Ala Pro Arg Asp Ile Ile Asn Gln Ile Leu
        355                 360                 365

Thr Ala Pro Ala Pro Ala Asp Leu Phe Phe Lys Asn Ala Asp Ile Asn
    370                 375                 380

Val Lys Phe Thr Gln Trp Phe Gln Ser Thr Leu Tyr Gly Trp Asn Ile
385                 390                 395                 400

Lys Leu Gly Thr Gln Thr Val Leu Ser Ser Arg Thr Gly Thr Ile Pro
                405                 410                 415

Pro Asn Tyr Leu Ala Tyr Asp Gly Tyr Tyr Ile Arg Ala Ile Ser Ala
            420                 425                 430

Cys Pro Arg Gly Val Ser Leu Ala Tyr Asn His Asp Leu Thr Thr Leu
        435                 440                 445

Thr Tyr Asn Arg Ile Glu Tyr Asp Ser Pro Thr Thr Glu Asn Ile Ile
    450                 455                 460

Val Gly Phe Ala Pro Asp Asn Thr Lys Asp Phe Tyr Ser Lys Lys Ser
465                 470                 475                 480
```

-continued

```
His Tyr Leu Ser Glu Thr Asn Asp Ser Tyr Val Ile Pro Ala Leu Gln
                485                 490                 495

Phe Ala Glu Val Ser Asp Arg Ser Phe Leu Glu Asp Thr Pro Asp Gln
            500                 505                 510

Ala Thr Asp Gly Ser Ile Lys Phe Ala Arg Thr Phe Ile Ser Asn Glu
        515                 520                 525

Ala Lys Tyr Ser Ile Arg Leu Asn Thr Gly Phe Asn Thr Ala Thr Arg
    530                 535                 540

Tyr Lys Leu Ile Ile Arg Val Arg Val Pro Tyr Arg Leu Pro Ala Gly
545                 550                 555                 560

Ile Arg Val Gln Ser Gln Asn Ser Gly Asn Asn Arg Met Leu Gly Ser
                565                 570                 575

Phe Thr Ala Asn Ala Asn Pro Glu Trp Val Asp Phe Val Thr Asp Ala
            580                 585                 590

Phe Thr Phe Asn Asp Leu Gly Ile Thr Thr Ser Ser Thr Asn Ala Leu
        595                 600                 605

Phe Ser Ile Ser Ser Asp Ser Leu Asn Ser Gly Glu Glu Trp Tyr Leu
    610                 615                 620

Ser Gln Leu Phe Leu Val Lys Glu Ser Ala Phe Thr Thr Gln Ile Asn
625                 630                 635                 640

Pro Leu Leu Lys


<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:j80

<400> SEQUENCE: 8

aataatatga tnaattttcc natgta                                          26


<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:j66

<400> SEQUENCE: 9

atgcattatt atggnaatng naatga                                          26


<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:j37

<400> SEQUENCE: 10

aatatngaaa tngcnacaag agatta                                          26


<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:JEG80

<400> SEQUENCE: 11
```

-continued

```
Met Gln Asn Asn Asn Phe Asn Thr Thr Glu Ile Asn Asn Met Ile Asn
 1               5                  10                  15

Phe Pro Met Tyr
            20


<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence:JEG70

<400> SEQUENCE: 12

Met Xaa Phe Ala Ser Tyr Gly Xaa Arg Asp Asn Glu Tyr Leu
  1               5                  10


<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence:JEG66

<400> SEQUENCE: 13

Met His Tyr Tyr Gly Asn Arg Asn Glu Tyr Asp Ile Leu Asn Ala
  1               5                  10                  15


<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:JEG37

<400> SEQUENCE: 14

Thr Ile Thr Asn Ile Glu Ile Ala Thr Arg Asp Tyr Thr Asn Xaa Asp
  1               5                  10                  15

Xaa Thr Gly Glu
            20


<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence:RIBOSOME
      BINDING SITE (FIGURE 5)

<400> SEQUENCE: 15

aaagaagagg g                                                        11
```